(12) United States Patent
Findlay et al.

(10) Patent No.: US 12,043,832 B2
(45) Date of Patent: Jul. 23, 2024

(54) METHODS AND COMPOSITIONS FOR REDUCING PATHOGENIC ISOFORMS

(71) Applicant: Washington University, St. Louis, MO (US)

(72) Inventors: Andrew Findlay, St. Louis, MO (US); Conrad Weihl, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 17/932,996

(22) Filed: Sep. 16, 2022

(65) Prior Publication Data

US 2023/0079754 A1 Mar. 16, 2023

Related U.S. Application Data

(60) Provisional application No. 63/245,108, filed on Sep. 16, 2021.

(51) Int. Cl.
*C12N 15/113* (2010.01)
*A61P 21/00* (2006.01)

(52) U.S. Cl.
CPC ............ *C12N 15/113* (2013.01); *A61P 21/00* (2018.01); *C12N 2310/11* (2013.01); *C12N 2310/14* (2013.01); *C12N 2310/3231* (2013.01); *C12N 2310/3233* (2013.01); *C12N 2310/341* (2013.01); *C12N 2320/33* (2013.01); *C12N 2320/34* (2013.01)

(58) Field of Classification Search
CPC .............. C12N 15/113; C12N 2310/11; C12N 2310/14; C12N 2310/3231; C12N 2310/3233; C12N 2310/341; C12N 2320/33; C12N 2320/34; A61P 21/00
See application file for complete search history.

(56) References Cited

U.S. PATENT DOCUMENTS

| 8,090,542 B2 * | 1/2012 | Khvorova | C12Y 113/12007 435/6.1 |
| 2019/0256821 A1 * | 8/2019 | August | A61K 35/34 |

OTHER PUBLICATIONS

Ruggieri et al, "DNAJB6 Myopathies: Focused Review on an Emerging and Expanding Group of Myopathies", Sep. 2016, Frontiers in Molecular Biosciences, vol. 3, pp. 1-9. (Year: 2016).*
Bengoechea et al, "Inhibition of DNAJ-HSP70 interaction improves strength in muscular dystrophy", Aug. 2020, The Journal of Clinical Investigation, vol. 130, pp. 4470-4484. (Year: 2020).*

\* cited by examiner

*Primary Examiner* — Brian Whiteman
*Assistant Examiner* — Stephanie L Sullivan
(74) *Attorney, Agent, or Firm* — Polsinelli PC

(57) ABSTRACT

Among the various aspects of the present disclosure is the provision of compositions and methods for selectively reducing pathogenic isoforms (e.g., DNAJB6) in a subject having a neuromuscular disorder. An aspect of the present disclosure provides for selectively reducing DNAJB6 in a subject having a neuromuscular disorder (e.g., limb-girdle muscular dystrophy D1 (LGMD-D1)) comprising administering an amount of a DNAJB6-targeting antisense oligonucleotide (ASO) sufficient to reduce the expression of DNAJB6 compared to the subject prior to being administered the DNAJB6-targeting ASO.

12 Claims, 30 Drawing Sheets
(25 of 30 Drawing Sheet(s) Filed in Color)
Specification includes a Sequence Listing.

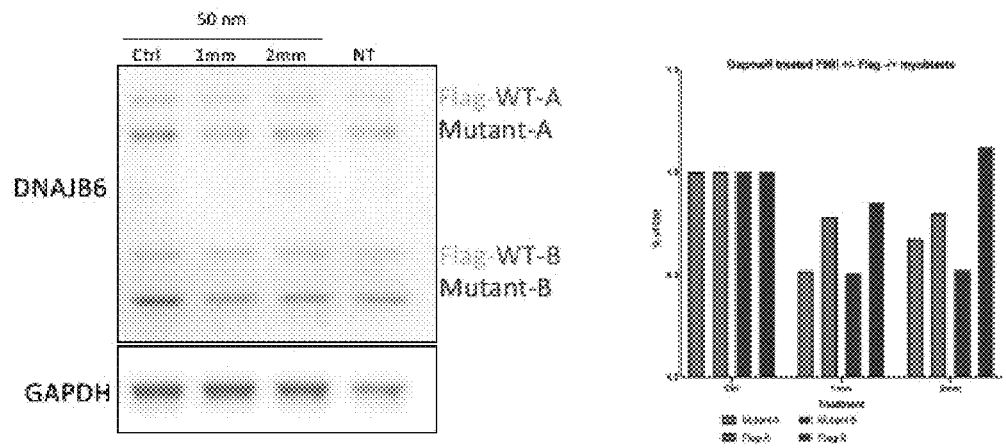
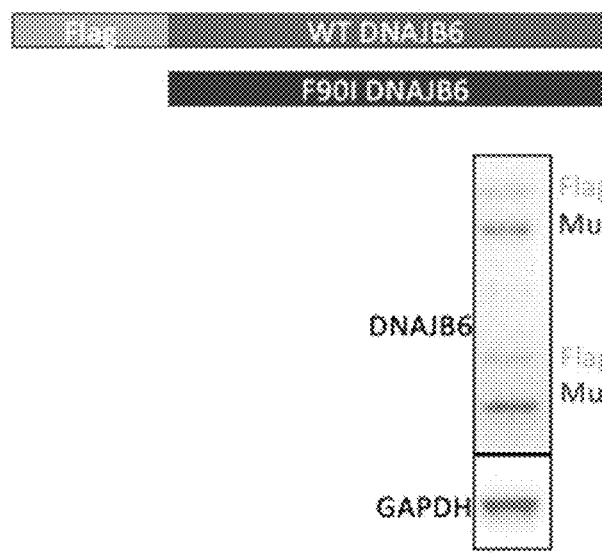
FIG. 9

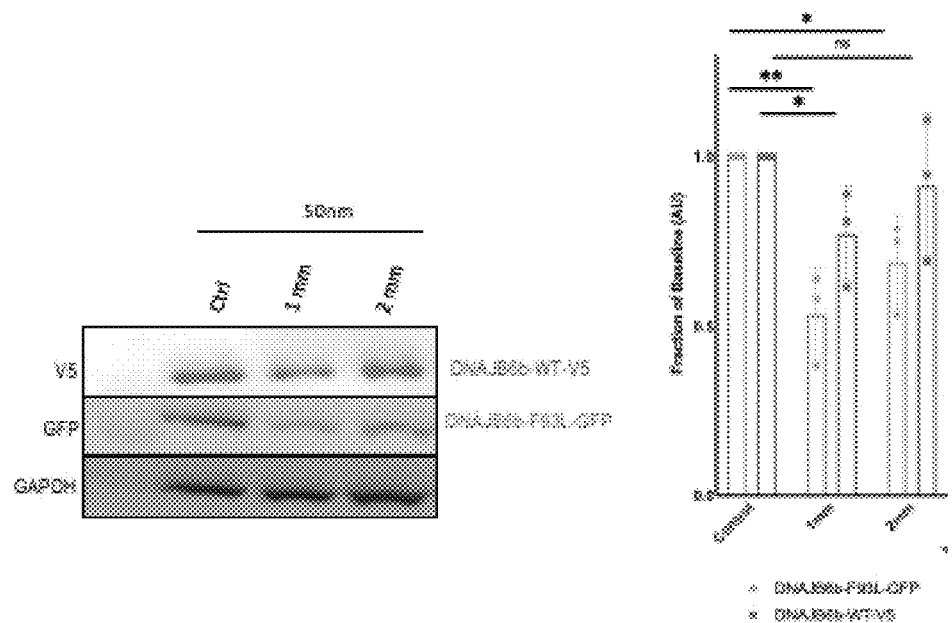
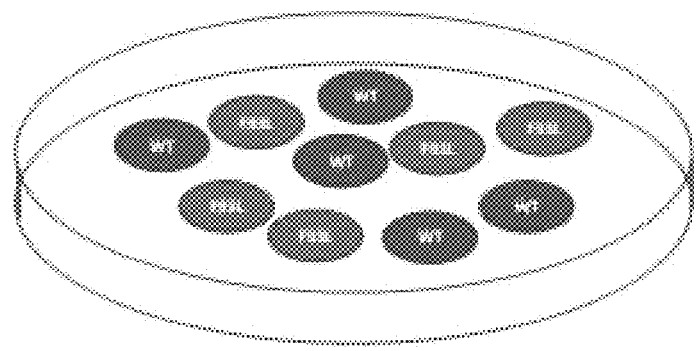
FIG. 11

FIG. 12 crispr/Cas9 Human DNAJB6 F93L and F89I cDNA specific knockdown
Cells:
-293Trex – hDNAJB6b-F93L-GFP
-293Trex – hDNAJB6b-F89I-GFP gRNA to selectively target F93L mutant allele:
Vgr5 (F93L 1 mismatch):
GAAGACATCATCTGGGTTACNGAG
Vgr5x (F93L 2 mismatch):
GAAGACATCATCTCGGTTACNGAG

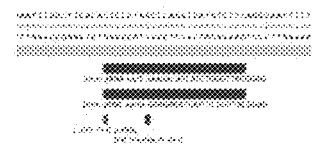

gRNA to selectively target F89I mutant allele:
Sp1 (F89I 1 mismatch):
TTTGACAGTCCATTTGAAATNGG
Sp2x (F89I 2 mismatch):
TTTGACAGTCCATTTGATATNGG

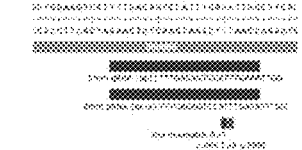

FIG. 15

```
                              SEQUENCE LISTING

Sequence total quantity: 61
SEQ ID NO: 1            moltype = DNA  length = 25
FEATURE                 Location/Qualifiers
source                  1..25
                        mol_type = other DNA
                        organism = synthetic construct
SEQUENCE: 1
tgcaccaaac acattcgcat ttatt                                                25

SEQ ID NO: 2            moltype = DNA  length = 25
FEATURE                 Location/Qualifiers
source                  1..25
                        mol_type = other DNA
                        organism = Mus musculus
SEQUENCE: 2
aataaatgcg aatgtgtttg gtgca                                                25

SEQ ID NO: 3            moltype = DNA  length = 49
FEATURE                 Location/Qualifiers
source                  1..49
                        mol_type = other DNA
                        organism = Mus musculus
SEQUENCE: 3
ggaattcatt ttgacagtcc atttgagttt ggcttcacat tccggaacc                      49

SEQ ID NO: 4            moltype = DNA  length = 49
FEATURE                 Location/Qualifiers
source                  1..49
                        mol_type = other DNA
                        organism = Mus musculus
SEQUENCE: 4
ggaattcatt ttgacagtcc atttgagatt ggcttcacat tccggaacc                      49

SEQ ID NO: 5            moltype = DNA  length = 16
FEATURE                 Location/Qualifiers
source                  1..16
                        mol_type = other DNA
                        organism = synthetic construct
SEQUENCE: 5
atttgagatt ggcttc                                                          16

SEQ ID NO: 6            moltype = DNA  length = 16
FEATURE                 Location/Qualifiers
source                  1..16
                        mol_type = other DNA
                        organism = synthetic construct
SEQUENCE: 6
tgagattggc ttgaca                                                          16

SEQ ID NO: 7            moltype = DNA  length = 16
FEATURE                 Location/Qualifiers
source                  1..16
                        mol_type = other DNA
                        organism = synthetic construct
SEQUENCE: 7
tcacactccg taaccg                                                          16

SEQ ID NO: 8            moltype = DNA  length = 16
FEATURE                 Location/Qualifiers
source                  1..16
                        mol_type = other DNA
                        organism = synthetic construct
SEQUENCE: 8
ggcttcacac tccgta                                                          16

SEQ ID NO: 9            moltype = DNA  length = 60
FEATURE                 Location/Qualifiers
source                  1..60
                        mol_type = other DNA
                        organism = Homo sapiens
SEQUENCE: 9
```

-continued

```
ggaagtcatt ttgacagtcc atttgaattt ggcttcacac tccgtaaccc agatgatgtc    60

SEQ ID NO: 10           moltype = DNA   length = 60
FEATURE                 Location/Qualifiers
source                  1..60
                        mol_type = other DNA
                        organism = Homo sapiens
SEQUENCE: 10
ggaagtcatt ttgacagtcc atttgaattt ggcttcacat tccgtaaccc agatgatgtc    60

SEQ ID NO: 11           moltype = DNA   length = 60
FEATURE                 Location/Qualifiers
source                  1..60
                        mol_type = other DNA
                        organism = Mus musculus
SEQUENCE: 11
ggaattcatt ttgacagtcc atttgagttt ggcttcacat tccggaaccc agatgatgtc    60

SEQ ID NO: 12           moltype = DNA   length = 60
FEATURE                 Location/Qualifiers
source                  1..60
                        mol_type = other DNA
                        organism = Mus musculus
SEQUENCE: 12
ggaattcatt ttgacagtcc atttgagatt ggcttcacat tccggaaccc agatgatgtc    60

SEQ ID NO: 13           moltype = DNA   length = 57
FEATURE                 Location/Qualifiers
source                  1..57
                        mol_type = other DNA
                        organism = synthetic construct
SEQUENCE: 13
tggaattcat tttgacagtc catttgagtt tggcttcaca ttccggaacc cagatga       57

SEQ ID NO: 14           moltype = DNA   length = 41
FEATURE                 Location/Qualifiers
source                  1..41
                        mol_type = other DNA
                        organism = synthetic construct
SEQUENCE: 14
attttgacag tccatttgag attggcttca cattccggaa c                        41

SEQ ID NO: 15           moltype = DNA   length = 21
FEATURE                 Location/Qualifiers
source                  1..21
                        mol_type = other DNA
                        organism = synthetic construct
SEQUENCE: 15
attggcttca cattccggaa c                                              21

SEQ ID NO: 16           moltype = DNA   length = 21
FEATURE                 Location/Qualifiers
source                  1..21
                        mol_type = other DNA
                        organism = synthetic construct
SEQUENCE: 16
gattggcttc acattccgga a                                              21

SEQ ID NO: 17           moltype = DNA   length = 21
FEATURE                 Location/Qualifiers
source                  1..21
                        mol_type = other DNA
                        organism = synthetic construct
SEQUENCE: 17
agattggctt cacattccgg a                                              21

SEQ ID NO: 18           moltype = DNA   length = 21
FEATURE                 Location/Qualifiers
source                  1..21
                        mol_type = other DNA
                        organism = synthetic construct
SEQUENCE: 18
gagattggct tcacattccg g                                              21

SEQ ID NO: 19           moltype = DNA   length = 21
FEATURE                 Location/Qualifiers
source                  1..21
                        mol_type = other DNA
                        organism = synthetic construct
```

```
SEQUENCE: 19
tgagattggc ttcacattcc g                                              21

SEQ ID NO: 20           moltype = DNA   length = 21
FEATURE                 Location/Qualifiers
source                  1..21
                        mol_type = other DNA
                        organism = synthetic construct
SEQUENCE: 20
ttgagattgg cttcacattc c                                              21

SEQ ID NO: 21           moltype = DNA   length = 21
FEATURE                 Location/Qualifiers
source                  1..21
                        mol_type = other DNA
                        organism = synthetic construct
SEQUENCE: 21
atttgagatt ggcttcacat t                                              21

SEQ ID NO: 22           moltype = DNA   length = 21
FEATURE                 Location/Qualifiers
source                  1..21
                        mol_type = other DNA
                        organism = synthetic construct
SEQUENCE: 22
catttgagat tggcttcaca t                                              21

SEQ ID NO: 23           moltype = DNA   length = 21
FEATURE                 Location/Qualifiers
source                  1..21
                        mol_type = other DNA
                        organism = synthetic construct
SEQUENCE: 23
ccatttgaga ttggcttcac a                                              21

SEQ ID NO: 24           moltype = DNA   length = 21
FEATURE                 Location/Qualifiers
source                  1..21
                        mol_type = other DNA
                        organism = synthetic construct
SEQUENCE: 24
gtccatttga gattggcttc a                                              21

SEQ ID NO: 25           moltype = DNA   length = 21
FEATURE                 Location/Qualifiers
source                  1..21
                        mol_type = other DNA
                        organism = synthetic construct
SEQUENCE: 25
agtccatttg agattggctt c                                              21

SEQ ID NO: 26           moltype = DNA   length = 21
FEATURE                 Location/Qualifiers
source                  1..21
                        mol_type = other DNA
                        organism = synthetic construct
SEQUENCE: 26
acagtccatt tgagattggc t                                              21

SEQ ID NO: 27           moltype = DNA   length = 21
FEATURE                 Location/Qualifiers
source                  1..21
                        mol_type = other DNA
                        organism = synthetic construct
SEQUENCE: 27
gacagtccat ttgagattgg c                                              21

SEQ ID NO: 28           moltype = DNA   length = 21
FEATURE                 Location/Qualifiers
source                  1..21
                        mol_type = other DNA
                        organism = synthetic construct
SEQUENCE: 28
tgacagtcca tttgagattg g                                              21

SEQ ID NO: 29           moltype = DNA   length = 21
FEATURE                 Location/Qualifiers
source                  1..21
                        mol_type = other DNA
```

-continued

```
                        organism = synthetic construct
SEQUENCE: 29
ttgacagtcc atttgagatt g                                              21

SEQ ID NO: 30           moltype = DNA  length = 21
FEATURE                 Location/Qualifiers
source                  1..21
                        mol_type = other DNA
                        organism = synthetic construct
SEQUENCE: 30
tttgacagtc catttgagat t                                              21

SEQ ID NO: 31           moltype = DNA  length = 21
FEATURE                 Location/Qualifiers
source                  1..21
                        mol_type = other DNA
                        organism = synthetic construct
SEQUENCE: 31
ttttgacagt ccatttgaga t                                              21

SEQ ID NO: 32           moltype = DNA  length = 21
FEATURE                 Location/Qualifiers
source                  1..21
                        mol_type = other DNA
                        organism = synthetic construct
SEQUENCE: 32
attttgacag tccatttgag a                                              21

SEQ ID NO: 33           moltype = DNA  length = 43
FEATURE                 Location/Qualifiers
source                  1..43
                        mol_type = other DNA
                        organism = synthetic construct
SEQUENCE: 33
cattttgaca gtccatttga gattggcttc acattccgga acc                      43

SEQ ID NO: 34           moltype = DNA  length = 22
FEATURE                 Location/Qualifiers
source                  1..22
                        mol_type = other DNA
                        organism = synthetic construct
SEQUENCE: 34
attggcttca cattccggaa cc                                             22

SEQ ID NO: 35           moltype = DNA  length = 22
FEATURE                 Location/Qualifiers
source                  1..22
                        mol_type = other DNA
                        organism = synthetic construct
SEQUENCE: 35
gattggcttc acattccgga ac                                             22

SEQ ID NO: 36           moltype = DNA  length = 22
FEATURE                 Location/Qualifiers
source                  1..22
                        mol_type = other DNA
                        organism = synthetic construct
SEQUENCE: 36
agattggctt cacattccgg aa                                             22

SEQ ID NO: 37           moltype = DNA  length = 22
FEATURE                 Location/Qualifiers
source                  1..22
                        mol_type = other DNA
                        organism = synthetic construct
SEQUENCE: 37
gagattggct tcacattccg ga                                             22

SEQ ID NO: 38           moltype = DNA  length = 22
FEATURE                 Location/Qualifiers
source                  1..22
                        mol_type = other DNA
                        organism = synthetic construct
SEQUENCE: 38
tgagattggc ttcacattcc gg                                             22

SEQ ID NO: 39           moltype = DNA  length = 22
FEATURE                 Location/Qualifiers
source                  1..22
```

```
                    mol_type = other DNA
                    organism = synthetic construct
SEQUENCE: 39
ttgagattgg cttcacattc cg                                           22

SEQ ID NO: 40       moltype = DNA   length = 22
FEATURE             Location/Qualifiers
source              1..22
                    mol_type = other DNA
                    organism = synthetic construct
SEQUENCE: 40
tttgagattg gcttcacatt cc                                           22

SEQ ID NO: 41       moltype = DNA   length = 22
FEATURE             Location/Qualifiers
source              1..22
                    mol_type = other DNA
                    organism = synthetic construct
SEQUENCE: 41
atttgagatt ggcttcacat tc                                           22

SEQ ID NO: 42       moltype = DNA   length = 22
FEATURE             Location/Qualifiers
source              1..22
                    mol_type = other DNA
                    organism = synthetic construct
SEQUENCE: 42
catttgagat tggcttcaca tt                                           22

SEQ ID NO: 43       moltype = DNA   length = 22
FEATURE             Location/Qualifiers
source              1..22
                    mol_type = other DNA
                    organism = synthetic construct
SEQUENCE: 43
ccatttgaga ttggcttcac at                                           22

SEQ ID NO: 44       moltype = DNA   length = 22
FEATURE             Location/Qualifiers
source              1..22
                    mol_type = other DNA
                    organism = synthetic construct
SEQUENCE: 44
tccatttgag attggcttca ca                                           22

SEQ ID NO: 45       moltype = DNA   length = 22
FEATURE             Location/Qualifiers
source              1..22
                    mol_type = other DNA
                    organism = synthetic construct
SEQUENCE: 45
gtccatttga gattggcttc ac                                           22

SEQ ID NO: 46       moltype = DNA   length = 22
FEATURE             Location/Qualifiers
source              1..22
                    mol_type = other DNA
                    organism = synthetic construct
SEQUENCE: 46
agtccatttg agattggctt ca                                           22

SEQ ID NO: 47       moltype = DNA   length = 22
FEATURE             Location/Qualifiers
source              1..22
                    mol_type = other DNA
                    organism = synthetic construct
SEQUENCE: 47
cagtccattt gagattggct tc                                           22

SEQ ID NO: 48       moltype = DNA   length = 22
FEATURE             Location/Qualifiers
source              1..22
                    mol_type = other DNA
                    organism = synthetic construct
SEQUENCE: 48
acagtccatt tgagattggc tt                                           22

SEQ ID NO: 49       moltype = DNA   length = 22
FEATURE             Location/Qualifiers
```

```
                        -continued source                  1..22
                        mol_type = other DNA
                        organism = synthetic construct
SEQUENCE: 49
gacagtccat ttgagattgg ct                                            22

SEQ ID NO: 50           moltype = DNA   length = 22
FEATURE                 Location/Qualifiers
source                  1..22
                        mol_type = other DNA
                        organism = synthetic construct
SEQUENCE: 50
tgacagtcca tttgagattg gc                                            22

SEQ ID NO: 51           moltype = DNA   length = 22
FEATURE                 Location/Qualifiers
source                  1..22
                        mol_type = other DNA
                        organism = synthetic construct
SEQUENCE: 51
ttgacagtcc atttgagatt gg                                            22

SEQ ID NO: 52           moltype = DNA   length = 22
FEATURE                 Location/Qualifiers
source                  1..22
                        mol_type = other DNA
                        organism = synthetic construct
SEQUENCE: 52
tttgacagtc catttgagat tg                                            22

SEQ ID NO: 53           moltype = DNA   length = 22
FEATURE                 Location/Qualifiers
source                  1..22
                        mol_type = other DNA
                        organism = synthetic construct
SEQUENCE: 53
ttttgacagt ccatttgaga tt                                            22

SEQ ID NO: 54           moltype = DNA   length = 22
FEATURE                 Location/Qualifiers
source                  1..22
                        mol_type = other DNA
                        organism = synthetic construct
SEQUENCE: 54
attttgacag tccatttgag at                                            22

SEQ ID NO: 55           moltype = DNA   length = 22
FEATURE                 Location/Qualifiers
source                  1..22
                        mol_type = other DNA
                        organism = synthetic construct
SEQUENCE: 55
cattttgaca gtccatttga ga                                            22

SEQ ID NO: 56           moltype = RNA   length = 24
FEATURE                 Location/Qualifiers
source                  1..24
                        mol_type = other RNA
                        organism = Homo sapiens
SEQUENCE: 56
aataaatgcg aatgtgttgg tgca                                          24

SEQ ID NO: 57           moltype = RNA   length = 23
FEATURE                 Location/Qualifiers
source                  1..23
                        mol_type = other RNA
                        organism = synthetic construct
SEQUENCE: 57
tttgacagtc catttgagat ngg                                           23

SEQ ID NO: 58           moltype = RNA   length = 23
FEATURE                 Location/Qualifiers
source                  1..23
                        mol_type = other RNA
                        organism = synthetic construct
SEQUENCE: 58
tttgacagtc catttgaaat ngg                                           23

SEQ ID NO: 59           moltype = RNA   length = 24
```

```
FEATURE             Location/Qualifiers
source              1..24
                    mol_type = other RNA
                    organism = synthetic construct
SEQUENCE: 59
gaagacatca tctgggttac ngag                                          24

SEQ ID NO: 60       moltype = RNA  length = 24
FEATURE             Location/Qualifiers
source              1..24
                    mol_type = other RNA
                    organism = synthetic construct
SEQUENCE: 60
gaagacatca tctcggttac ngag                                          24

SEQ ID NO: 61       moltype = RNA  length = 23
FEATURE             Location/Qualifiers
source              1..23
                    mol_type = other RNA
                    organism = synthetic construct
SEQUENCE: 61
tttgacagtc catttgatat ngg                                           23
```

METHODS AND COMPOSITIONS FOR REDUCING PATHOGENIC ISOFORMS

CROSS REFERENCE TO RELATED APPLICATIONS

This application claims the benefit of U.S. Provisional Application No. 63/245,108, filed Sep. 16, 2021 the disclosure of which is herein incorporated by reference in its entirety.

GOVERNMENTAL RIGHTS

This invention was made with government support under AR068797 and AR075894 awarded by National Institutes of Health. The government has certain rights in the invention.

REFERENCE TO SEQUENCE LISTING

This application contains a Sequence Listing that has been submitted in ASCII format via EFS-Web and is hereby incorporated by reference in its entirety. The ASCII copy, created on Sep. 16, 2022, is named 047563_737649_sequence.xml, and is 57,344 bytes in size.

FIELD OF THE TECHNOLOGY

The present disclosure generally relates to methods and compositions for reducing pathogenic isoforms of molecular chaperones for the therapeutic application in muscular dystrophy.

BACKGROUND

Mutations in the DNAJB6 gene have been associated with the autosomal dominant limb girdle muscular dystrophy type 1D (LGMD1D), a disorder characterized by abnormal protein aggregates and rimmed vacuoles in muscle fibers. DNAJB6 is a ubiquitously expressed Hsp40 co-chaperone characterized by a J domain that specifies Hsp70 functions in the cellular environment. DNAJB6 is also a potent inhibitor of expanded polyglutamine (polyQ) aggregation preventing aggregate toxicity in cells. In DNAJB6-mutated patients this anti-aggregation property is significantly reduced, albeit not completely lost. To elucidate the pathogenetic mechanisms underlying the DNAJB6-related myopathy, animal models have been created showing that, indeed, conditional muscular expression of a DNAJB6 mutant in the mouse causes a LGMD1D myofibrillary muscle tissue phenotype. Both mutations and phenotypes reported until recently were rather homogeneous, being exclusively missense mutations of a few amino acids of the protein G/F domain, and with a phenotype characterized by adult-onset slowly progressive muscular dystrophy predominantly affecting proximal muscles. Lately, several novel mutations and new phenotypes of DNAJB6 have been described. These mutations once more affect the G/F domain of DNAJB6 with missense changes and a splice site mutation; and the phenotypes include childhood onset and distal involvement of muscles, or childhood-onset LGMD1D with loss of ambulation in early adulthood and respiratory involvement. Thus, the spectrum of DNAJB6-related phenotypes is widening. Although our knowledge about the role of DNAJB6 in the pathogenesis of muscle diseases has made great progression, several questions remain unsolved, including possible therapeutic strategies for DNAJB6-related myopathies.

Therefore a need exists in the art for a safe and effective therapeutics for the treatment of DNAJB6-related myopathies.

SUMMARY

Among the various aspects of the present disclosure is the provision of compositions and methods for selectively reducing pathogenic isoforms of DNAJB6 in a subject having a DNAJB6-related myopathy.

An aspect of the present disclosure provides for a method of selectively reducing DNAJB6 in a subject comprising administering an amount of a DNAJB6-targeting antisense oligonucleotide (ASO) sufficient to reduce the expression of DNAJB6 compared to the subject prior to being administered the DNAJB6-targeting ASO.

Another aspect of the present disclosure provides for a method of treating a neuromuscular disorder (e.g., limb-girdle muscular dystrophy D1 (LGMD-D1)) comprising administering an antisense oligonucleotide (ASO) targeting DNAJB6 to a subject, wherein the ASO reduces DNAJB6 isoforms (such as DNAJB6b).

In some embodiments, the neuromuscular disorder is associated with overexpression of DNAJB6.

In some embodiments, the ASO reduces or eliminates pathogenic isoform transcripts.

In some embodiments, the ASO increases intron 8 splicing.

In some embodiments, the ASO targets the proximal polyadenylation signal (PAS) downstream of exon 8 of the DNAJB6 gene.

In some embodiments, the ASO sequence comprises TGCACCAAACACATTCGCATTTATT (SEQ ID NO: 1); or a sequence at least about 85%, 90%, 95%, or 99% identical to SEQ ID NO: 1 having DNAJB6 reducing activity.

In some embodiments, the ASO sequence targets the DNAJB6 sequence. In some embodiments, the ASO is targeting (mouse DNAJB6) has a sequence comprising AATAAATGCGAATGTGTTTGGTGCA (SEQ ID NO: 2) (which is the reverse complement of the ASO sequence SEQ ID NO: 1).

In some embodiments, the DNAJB6-related myopathy is not a recessively inherited disorder.

In some embodiments, the DNAJB6-related myopathy is a dominantly inherited disorder.

In some embodiments, the DNAJB6-related myopathy is limb girdle muscular dystrophy (LGMD).

In some embodiments, the ASO selectively reduce levels of DNAJB6b isoform expression.

Yet another aspect of the present disclosure provides for a pharmaceutical composition comprising an ASO comprising SEQ ID NO: 1; or a sequence at least about 85%, 90%, 95%, or 99% identical to SEQ ID NO: 1 having DNAJB6 reducing activity.

While multiple embodiments are disclosed, still other embodiments of the present invention will become apparent to those skilled in the art from the following detailed description, which shows and describes illustrative embodiments of the invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 9 shows a therapeutic strategy for allele specific knockdown Myoblasts: Knock-in F90I+/−, Flag−/+ ASOs: LNA-GapmeR. (SEQ ID NOs: 3, 4, 5 and 6).

FIG. 11 shows therapeutic strategy for allele specific knockdown Stable Cells: DNAJB6b-WT-V5, DNAJB6b-F93L-GFP ASOs: LNA-GapmeR.

FIG. 12 shows 21mer vs 22mer siRNA Off Target analysis relative to a wildtype sequence (SEQ ID NO: 13).

FIG. 15 shows CRISPR/Cas9 Human DNAJB6 F93L and F89I cDNA specific knockdown. (SEQ ID NOs: 58, 59, 60, and 61).

DETAILED DESCRIPTION

Figure 1A:
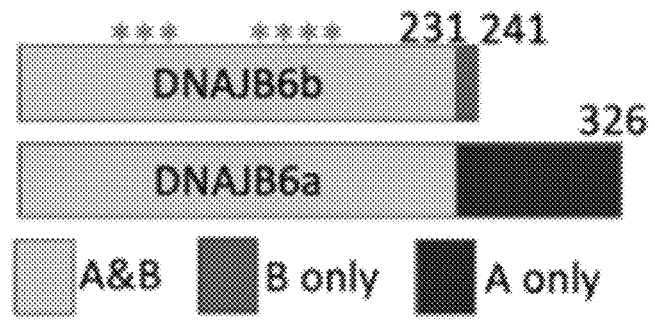
FIG. 1A shows a schematic of DNAJB6 isoforms and locations of disease-causing mutations (red asterisks), which reside within regions shared by both isoforms. DNAJB6b contains only 10 unique residues.

The present disclosure is based, at least in part, on the discovery of compositions and methods for treating DNAJb6-related myopathies through isoform specific knockdown of DNAJB6b or targeted knockdown of the mutant allele. Both address the toxic gain of function mechanism, yet avoid the damaging effects of complete DNAJB6 loss of function (e.g. complete knockout).

The disclosure shows ASOs targeting and selectively reducing DNAJB6b can treat patients having limb-girdle muscular dystrophy D1 (LGMD-D1). Limb girdle muscular dystrophy type D1 (LGMD-D1) is due to mutations in a gene called DNAJB6. DNAJB6 has two isoforms, one of which (DNAJB6b) is thought to be pathogenic. The Applicant has designed antisense oligonucleotides (specifically, morpholinos, which alter splicing of RNA) to selectively reduce levels of the pathogenic DNAJB6b isoform. This was achieved in cell culture and in vivo in mouse models. Thus, the present disclosure provides methods and compositions for the selective reduction of DNAJB6b. In particular the present disclosure provides the therapeutic strategies to selectively reduce DNAJB6b for subjects in need thereof.

The applicants have developed a therapeutic knockdown strategy (allele specific knockdown, not isoform specific knockdown), which targets different sequences of DNAJB6. This knockdown strategy aims to selectively reduce the mutant DNAJB6 allele and leave the WT allele intact. Using a chemistry called LNA (locked nucleic acid) gapmers—a type of ASO, to achieve allele specific knockdown. siRNA were developed to selectively knockdown the mutant allele as well. In addition to allele specific knockdown, Applicant shows allele specific knockout using CRISPR/Cas9 to be useful.

Disclosed are components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to a number of molecules of the compound are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Various aspects of the invention are described in further detail in the following sections.

(I) Compositions

The present disclosure provides DNAJB6 modulating agents. In some embodiments, the DNAJB6 modulating agent is antisense oligonucleotide (ASO) targeting DNAJB6 for reducing of DNAJB6 isoforms (such as pathogenic isoforms, e.g., DNAJB6b). As described herein, a DNAJB6-targeting antisense oligonucleotide (ASO) can be useful for the treatment of DNAJB6-related myopathies. A DNAJB6-targeting ASO modulation agent can be used to specifically reduce/eliminate DNAJB6 isoform activity and/or expression (e.g., DNAJB6b or mutant isoform) while not significantly modulating the expression and/or activity of non-pathogenic DNAJB6 isoforms (e.g., DNAJB6a or wild-type unmutated DNAJB6). For example, a DNAJB6-targeting antisense oligonucleotide (ASO) can be a morpholino, which alters splicing of RNA, a locked nucleic acid and/ siRNA which selectively targets mutant DNAJB6 (e.g. F93L, F89I, and/or P96R). Processes for making ASOs can be carried out in accordance with Zhou et al. 2016 Methods Mol Biol. 1402:199-213. Except as otherwise noted herein, therefore, the process of the present disclosure can be carried out in accordance with such processes.

In some embodiments, a DNAJB6 modulating agent of the disclosure is an ASO targeting a DNAJB6 sequence according to the present disclosure. In some embodiments, a DNAJB6 modulating agent of the disclosure targets DNAJB6b isoform in a specific manner, for example, targets the DNAJB6b isoform without significantly modulating the expression of the DNAJB6a isoform. In some embodiments, a DNAJB6 modulating agent of the disclosure targets DNAJB6 in an allele specific manner, for example, targets a mutant DNAJB6 allele (e.g., F93L, F89I, and P96R) without significantly modulating the expression of a wild-type, unmutated, DNAJB6 allele.

In some embodiments, an ASO according to the present disclosure targets 8-25 consecutive nucleotides within SEQ ID NO: 2, 7, 8, 9, 10, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or 56. In some embodiment, an ASO according to the present disclosure targets a targets 8-25 consecutive nucleotides within SEQ ID NO: 2, 7, 8, 9, 10, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or 56 with at least 90%, 91%, 92%, 93%, 94%, 95%, 96%, 97%, 98%, or at least 99% sequence identity to the 8-25 consecutive nucleotides. In some embodiments, the ASO targets a proximal polyadenylation signal (PAS) downstream of exon 8 of a DNAJB6 gene. In certain embodiments, the ASO targeting target the proximal polyadenylation signal (PAS) downstream of exon 8 increases intron 8 splicing. In certain embodiments, an antisense oligonucleotide comprises 8-25 nucleotides at least 90%, 91%, 92%, 93%, 94%,95%, 96%, 97%, 98%, or at least 99% complementary to a proximal polyadenylation signal (PAS) downstream of exon 8 of a DNAJB6 gene. In certain embodiments, an ASO sequence of the present disclosure comprises, consists essentially of or consists of the nucleotide sequence of SEQ ID NO: 1. In certain embodiments, an ASO sequence of the present disclosure comprises, consists essentially of or consists of the nucleotide sequence that is the reverse complement of SEQ ID NO: 56.

In some embodiments, the DNAJB6 modulating agent is an locked nucleic acid (LNA) to achieve allele specific knockdown. In some embodiments, the DNAJB6 allele targeted encodes a F93L mutation. In some embodiment, an ASO sequence of the present disclosure comprises, consists essentially of or consists of the nucleotide sequence that is the reverse complement of SEQ ID NO: 7 or 8.

In some embodiments, the DNAJB6 modulating agent is a shRNA or siRNA. In some embodiments, the DNAJB6 allele targeted encodes a F89I mutation. In some embodiment, the shRNA or siRNA targets the nucleotide sequence of SEQ ID NO: 23, 24, 25, 26, 43, 44, 45, 46, 47, or 48.

A Morpholino, also known as a Morpholino oligomer and as a phosphorodiamidate Morpholino oligomer (PMO), is a type of oligomer molecule (colloquially, an oligo) used in molecular biology to modify gene expression. Its molecular structure can be DNA bases attached to a backbone of methylenemorpholine rings linked through phosphorodiamidate groups. Morpholinos can block access of other molecules to small (~25 base) specific sequences of the base-pairing surfaces of ribonucleic acid (RNA). Morpholinos are used as research tools for reverse genetics by knocking down gene function. Morpholino antisense oligomers can be nucleic acid analogs. The word Morpholino oligos can be referred to as PMO (for phosphorodiamidate morpholino oligomer), especially in medical literature. Vivo-Morpholinos and PPMO can be modified forms of Morpholinos with chemical groups covalently attached to facilitate entry into cells. Gene knockdown can be achieved by preventing cells from making a targeted protein.

An antisense oligonucleotide of the disclosure may be synthesized using chemical synthesis and enzymatic ligation reactions using procedures known in the art. For example, an oligonucleotide (e.g., an antisense oligonucleotide) may be chemically synthesized using naturally occurring ribonucleotides, deoxyribonucleotides, variously modified nucleotides designed to increase the biological stability of the molecules or to increase the physical stability of the duplex formed between the antisense and sense nucleic acids, or combinations thereof. For example, phosphorothioate derivatives and acridine substituted nucleotides can be used. Other examples of modified nucleotides which may be used to generate an antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylam inomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylam inomethyluracil, 5-methoxyaminomethyl-2-thiouracil, beta-D -mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, que-osine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-aino -3-N-2-carboxypropyl) uracil, (acp3)w, and 2,6-diaminopurine. Alternatively, the oligonucleotide may be produced biologically using an expression vector into which a nucleic acid has been subcloned in an antisense orientation.

In certain embodiments, antisense oligonucleotides provided herein may include one or more modifications to a nucleobase, sugar, and/or internucleoside linkage, and as such is a modified oligonucleotide. A modified nucleobase, sugar, or internucleoside linkage may be selected over an unmodified form because of desirable properties such as, for example, enhanced cellular uptake, enhanced affinity for other oligonucleotides or nucleic acid targets, and increased stability in the presence of nucleases. In certain embodiments, a modified nucleoside is a sugar-modified nucleoside. In certain such embodiments, sugar-modified nucleosides may further comprise a natural or modified heterocyclic base moiety or natural or modified internucleoside linkage and may include further modifications independent from the sugar modification. In certain embodiments, a sugar modified nucleoside is a 2'-modified nucleoside, wherein the sugar ring is modified at the 2' carbon from natural ribose or 2'-deoxy-ribose. In certain embodiments, a 2'-modified nucleoside comprises a 2'-substituent group selected from F, O—$CH_3$, and $OCH_2CH_2OCH_3$. In certain embodiments, a 2'-modified nucleoside has a bicyclic sugar moiety. In certain embodiments, a bicyclic sugar moiety comprises a bridge group between the 2' and the 4' carbon atoms.

In certain embodiments, a modified oligonucleotide comprises one or more internucleoside modifications. In certain such embodiments, each internucleoside linkage of an oligonucleotide is a modified internucleoside linkage. In certain embodiments, a modified internucleoside linkage comprises a phosphorus atom.

In certain embodiments, a modified oligonucleotide comprises at least one phosphorothioate internucleoside linkage. In preferred embodiments, each internucleoside linkage of a modified oligonucleotide is a phosphorothioate internucleoside linkage.

In certain embodiments, a modified oligonucleotide comprises one or more modified nucleobases. In certain embodiments, a modified oligonucleotide comprises one or more 5-methylcytosines. In certain embodiments, each cytosine of a modified oligo-nucleotide comprises a 5-methylcytosine.

In certain embodiments, a modified nucleobase is selected from 5-hydroxymethyl cytosine, 7-deazaguanine and 7-deazaadenine. In certain embodiments, a modified nucleobase is selected from 7-deazaadenine, 7-deazaguanosine, 2-aminopyridine and 2-pyridone.

In some embodiments, the antisense molecules of the disclosure may be modified at the base moiety, sugar moiety or phosphate backbone to improve, e.g., the stability, hybridization, or solubility of the molecule. By way of another example, the deoxyribose phosphate backbone of the nucleic acids may be modified to generate peptide nucleic acids (see Hyrup et al. (1996) Bioorganic & Medicinal Chemistry 4(I):5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of a PNA has been shown to allow for specific hybridization to DNA and RNA under conditions of low ionic strength. The synthesis of PNA oligomers may be performed using standard solid phase peptide synthesis protocols as described in Hyrup et al. (1996) supra; Perry-O'Keefe et al. (1996) Proc. Natl. Acad. Sci. USA 93:14670-675.

PNAs of DNAJB6 may be used for therapeutic applications. PNAs of DNAJB6 may also be used in the analysis of single base pair mutations in a gene by PNA-directed PCR clamping; as artificial restriction enzymes when used in combination with other enzymes, such as S1 nucleases (Hyrup (1996) supra); or as probes or primers for DNA sequence and hybridization (Hyrup (1996) supra; Perry-O'Keefe et al. (1996) Proc. Natl. Acad. Sci. USA 93: 14670-675).

In other embodiments, the oligonucleotides of the invention may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553-6556; Lemaitre et al. (1987) Proc. Natl. Acad. Sci. USA 84:648-652; PCT Publication No. WO 88/09810) or the blood-brain barrier (see, e.g., PCT Publication No. WO 89/10134). In addition, oligonucleotides may be modified with hybridization-triggered cleavage agents (see, e.g., Krol et al. (1988) Bio/Techniques 6:958-976) or intercalating agents (see, e.g., Zon (1988) Pharm. Res. 5:539-549). To this end, the oligonucleotide may be conjugated to another molecule, e.g., a peptide, hybridization triggered cross-linking agent, transport agent, hybridization-triggered cleavage agent, etc.

In certain embodiments, an antisense oligonucleotide of the invention is synthesized with a full phosphorothioate backbone with alternating blocks of 2'-MOE and 2'fluoro sugar-modified nucleosides.

The DNAJB6 modulating agent (also referred to herein as "active compounds") of the invention may be incorporated into pharmaceutical compositions suitable for administration. Such compositions typically comprise the agent and a pharmaceutically acceptable carrier. As used herein, the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds may also be incorporated into the compositions.

As another example, RNA (e.g., long noncoding RNA (lncRNA)) can be targeted with antisense oligonucleotides (ASOs) as a therapeutic. Processes for making ASOs targeted to RNAs are well known; see e.g. Zhou et al. 2016 Methods Mol Biol. 1402:199-213. Except as otherwise noted herein, therefore, the process of the present disclosure can be carried out in accordance with such processes. Methods of downregulation or silencing genes are known in the art. For example, expressed protein activity can be down-regulated or eliminated using antisense oligonucleotides (ASOs), protein aptamers, nucleotide aptamers, and RNA interference (RNAi) (e.g., small interfering RNAs (siRNA), short hairpin RNA (shRNA), and micro RNAs (miRNA) (see e.g., Rinaldi and Wood (2017) Nature Reviews Neurology 14, describing ASO therapies; Fanning and Symonds (2006) Handb Exp Pharmacol. 173, 289-303G, describing hammerhead ribozymes and small hairpin RNA; Helene, et al. (1992) Ann. N.Y. Acad. Sci. 660, 27-36; Maher (1992) Bioassays 14(12): 807-15, describing targeting deoxyribonucleotide sequences; Lee et al. (2006) Curr Opin Chem Biol. 10, 1-8, describing aptamers; Reynolds et al. (2004) Nature Biotechnology 22(3), 326-330, describing RNAi; Pushparaj and Melendez (2006) Clinical and Experimental Pharmacology and Physiology 33(5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, TX; Sigma Aldrich, MO; Invitrogen). Several siRNA molecule design programs using a variety of algorithms are known to the art (see e.g., Cenix algorithm, Ambion; BLOCK-iT™ RNAi Designer, Invitrogen; siRNA Whitehead Institute Design Tools, Bioinofrmatics & Research Computing). Traits influential in defining optimal siRNA sequences include G/C content at the termini of the siRNAs, Tm of specific internal domains of the siRNA, siRNA length, position of the target sequence within the CDS (coding region), and nucleotide content of the 3' over-hangs.

As another example, an DNAJB6 inhibiting agent can be an sgRNA targeting DNAJB6. Inhibiting DNAJB6 can be performed by genetically modifying DNAJB6 in a subject or genetically modifying a subject to reduce or prevent expression of the DNAJB6 gene (e.g. by disrupting the DNAJB6 locus), such as through the use of CRISPR-Cas9 or analogous technologies, wherein, such modification reduces or prevents DNAJB6 expression. Processes for genome editing are well known; see e.g. Aldi 2018 Nature Communications 9(1911). Except as otherwise noted herein, therefore, the process of the present disclosure can be carried out in accordance with such processes.

For example, genome editing can comprise CRISPR/Cas9, CRISPR-Cpf1, TALEN, or ZNFs. Adequate blockage of DNAJB6 by genome editing can result in protection from proliferative diseases, cancer.

As an example, clustered regularly interspaced short palindromic repeats (CRISPR)/CRISPR-associated (Cas) systems are a new class of genome-editing tools that target desired genomic sites in mammalian cells. Recently published type II CRISPR/Cas systems use Cas9 nuclease that is targeted to a genomic site by complexing with a synthetic guide RNA that hybridizes to a 20-nucleotide DNA sequence and immediately preceding an NGG motif recognized by Cas9 (thus, a (N)2ONGG target DNA sequence). This results in a double-strand break three nucleotides upstream of the NGG motif. The double strand break instigates either non-homologous end-joining, which is error prone and conducive to frameshift mutations that knock out gene alleles, or homology-directed repair, which can be exploited with the use of an exogenously introduced double strand or single-strand DNA repair template to knock in or correct a mutation in the genome. Thus, genomic editing, for example, using CRISPR/Cas systems could be useful tools for therapeutic applications for cancer to target epithelial cells by the removal of DNAJB6 activity (e.g., downregulate DNAJB6).

For example, the methods as described herein can comprise a method for altering a target polynucleotide sequence in a cell comprising contacting the polynucleotide sequence with a clustered regularly interspaced short palindromic repeats-associated (Cas) protein. In some embodiments, the gRNA for use according to the disclosure, comprises the nucleic acid sequence of SEQ ID NO: 58 or 59.

The nucleic acid molecules of the invention may be inserted into vectors and used as gene therapy vectors. Gene therapy vectors may be delivered to a subject by, for example, intravenous injection, local administration (U.S. Pat. No. 5,328,470) or by stereotactic injection (see, e.g., Chen et al. (1994) Proc. Natl. Acad. Sci. USA 91:3054-3057). The pharmaceutical preparation of the gene therapy vector may include the gene therapy vector in an acceptable diluent, or can comprise a slow release matrix in which the gene delivery vehicle is imbedded.

The gene therapy vectors of the invention may be either viral or non-viral. Examples of plasmid-based, non-viral vectors are discussed in Huang et al. (1999) Nonviral Vectors for Gene Therapy. A modified plasmid is one example of a non-viral gene delivery system. Peptides, proteins (including antibodies), and oligonucleotides may be stably conjugated to plasmid DNA by methods that do not interfere with the transcriptional activity of the plasmid (Zelphati et al. (2000) BioTechniques 28:304-315). The attachment of proteins and/or oligonucleotides may influence the delivery and trafficking of the plasmid and thus render it a more effective pharmaceutical composition.

Another aspect of the present disclosure provides nucleic acids encoding any of the DNAJB6-targeting antisense oligonucleotide (ASO) described above. The nucleic acid can be DNA or RNA. In one embodiment the DNA can be present in a vector. The nucleic acid sequences which encode the dominant negative molecule of the invention can be operatively linked to expression control sequences. "Operatively linked" refers to a juxtaposition wherein the components so described are in a relationship permitting them to function in their intended manner. An expression control sequence operatively linked to a coding sequence is achieved under conditions compatible with the expression control sequences. As used herein, the expression control sequences refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, and maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

In one aspect, the present disclosure provides for a vector comprising a nucleic acid sequence encoding for a DNAJB6-targeting antisense oligonucleotide (ASO). In one aspect, the present disclosure is predicated, at least in part, on the ability of adeno-associated virus (AAV) vectors to be safely administered to humans and to provide persistent expression of an ASO. The invention provides an adeno-associated virus (AAV) vector which comprises, consists essentially of, or consists of a nucleic acid sequence encoding a DNAJB6-targeting antisense oligonucleotide (ASO). When the AAV vector consists essentially of a nucleic acid sequence encoding an arginine-degrading enzyme polypeptide, additional components can be included that do not materially affect the AAV vector (e.g., genetic elements such as poly(A) sequences or restriction enzyme sites that facilitate manipulation of the vector in vitro). When the AAV vector consists of a nucleic acid sequence encoding an DNAJB6-targeting antisense oligonucleotide (ASO), the AAV vector does not comprise any additional components (i.e., components that are not endogenous to AAV and are not required to effect expression of the nucleic acid sequence to thereby provide the DNAJB6-targeting antisense oligonucleotide (ASO)).

Adeno-associated virus is a member of the Parvoviridae family and comprises a linear, single-stranded DNA genome of less than about 5,000 nucleotides. AAV re-quires co-infection with a helper virus (i.e., an adenovirus or a herpes virus), or expression of helper genes, for efficient replication. AAV vectors used for administration of therapeutic nucleic acids typically have approximately 96% of the parental genome deleted, such that only the terminal repeats (ITRs), which contain recognition signals for DNA replication and packaging, remain. This eliminates immunologic or toxic side effects due to expression of viral genes. In addition, delivering specific AAV proteins to producing cells enables integration of the AAV vector comprising AAV ITRs into a specific region of the cellular genome, if desired (see, e.g., U.S. Pat. Nos. 6,342,390 and 6,821,511). Host cells comprising an integrated AAV genome show no change in cell growth or morphology (see, for example, U.S. Pat. No. 4,797,368).

The AAV ITRs flank the unique coding nucleotide sequences for the non-structural replication (Rep) proteins and the structural capsid (Cap) proteins (also known as virion proteins (VPs)). The terminal 145 nucleotides are self-complementary and are organized so that an energetically stable intramolecular duplex forming a T-shaped hairpin may be formed. These hairpin structures function as an origin for viral DNA replication by serving as primers for the cellular DNA polymerase complex. The Rep genes encode the Rep proteins Rep78, Rep68, Rep52, and Rep40. Rep78 and Rep68 are transcribed from the p5 promoter, and Rep 52 and Rep40 are transcribed from the p19 promoter. The Rep78 and Rep68 proteins are multifunctional DNA binding proteins that perform helicase and nickase functions during productive replication to allow for the resolution of AAV termini (see, e.g., Im et al., Cell, 61: 447-57 (1990)). These proteins also regulate transcription from endogenous AAV promoters and promoters within helper viruses (see, e.g., Pereira et al., J. Virol., 71: 1079-1088 (1997)). The other Rep proteins modify the function of Rep78 and Rep68. The cap genes encode the capsid proteins VP1, VP2, and VP3. The cap genes are transcribed from the p40 promoter. In a particular embodiment, the AAV contains a pair of inverted terminal repeats (ITRs) which flank at least one cassette containing a promoter which directs cell-specific expression (e.g. hepatocytes) operably linked to a heterologous gene. Heterologous in this context refers to any nucleotide sequence or gene which is not native to the AAV or B19 parvovirus (e.g. an arginine-degrading enzyme). Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference in its entirety for material related to the AAV vector.

As used herein, the term "AAV vector" means a vector derived from an adeno-associated virus serotype. In non-limitation examples AAV vectors include, AAV1, AAV2, AAV3, AAV4, AAV5, AAV6, AAV7, AAV8, AAV9, and mutated forms thereof. AAV vectors can have one or more of the AAV wild-type genes deleted in whole or part, preferably the rep and/or cap genes, but retain functional flanking ITR sequences. De-spite the high degree of homology, the different serotypes have tropisms for different tissues. In an exemplary embodiment, the AAV vector is AAV9.

An AAV vector, as disclosed herein, can be generated using any AAV serotype known in the art. Several AAV serotypes and over 100 AAV variants have been isolated from adenovirus stocks or from human or nonhuman primate tissues (reviewed in, e.g., Wu et al., Molecular Therapy, 14(3): 316-327 (2006)). Generally, the AAV serotypes have genomic sequences of significant homology at the nucleic acid sequence and amino acid sequence levels, such that different serotypes have an identical set of genetic functions, produce virions which are essentially physically and functionally equivalent, and replicate and assemble by practically identical mechanisms. AAV serotypes 1-6 and 7-9 are defined as "true" serotypes, in that they do not efficiently cross-react with neutralizing sera specific for all other existing and characterized serotypes. In contrast, AAV serotypes 6, 10 (also referred to as Rh10), and 11 are considered "variant" serotypes as they do not adhere to the definition of a "true" serotype. AAV serotype 2 (AAV2) has been used extensively for gene therapy applications due to its lack of pathogenicity, wide range of infectivity, and ability to establish long-term transgene expression (see, e.g., Carter, B. J., Hum. Gene Ther., 16: 541-550 (2005); and Wu et al., supra). Genome sequences of various AAV serotypes and comparisons thereof are disclosed in, for example, GenBank Accession numbers U89790, J01901, AF043303, and AF085716; Chiorini et al., J. Virol., 71: 6823-33 (1997); Srivastava et al., J. Virol., 45: 555-64 (1983); Chiorini et al., J. Virol., 73: 1309-1319 (1999); Rutledge et al., J. Virol., 72: 309-319 (1998); and Wu et al., J. Virol., 74: 8635-47 (2000)).

AAV rep and ITR sequences are particularly conserved across most AAV serotypes. For example, the Rep78 proteins of AAV2, AAV3A, AAV3B, AAV4, and AAV6 are reportedly about 89-93% identical (see Bantel-Schaal et al., J. Virol., 73(2): 939-947 (1999)). It has been reported that AAV serotypes 2, 3A, 3B, and 6 share about 82% total nucleotide sequence identity at the genome level (Bantel-Schaal et al., supra). Moreover, the rep sequences and ITRs of many AAV serotypes are known to efficiently cross-complement (i.e., functionally substitute) corresponding sequences from other serotypes during production of AAV particles in mammalian cells.

Generally, the cap proteins, which determine the cellular tropicity of the AAV particle, and related cap protein-encoding sequences, are significantly less conserved than Rep genes across different AAV serotypes. In view of the ability Rep and ITR sequences to cross-complement corresponding sequences of other serotypes, the AAV vector can comprise a mixture of serotypes and thereby be a "chimeric" or "pseudo-typed" AAV vector. A chimeric AAV vector typically comprises AAV capsid proteins de-rived from two or more (e.g., 2, 3, 4, etc.) different AAV serotypes. In contrast, a pseudo-typed AAV vector comprises one or more ITRs of one AAV serotype packaged into a capsid of another AAV serotype. Chimeric and pseudotyped AAV vectors are further described in, for example, U.S. Pat. No. 6,723,551; Flotte, Mol. Ther., 13(1): 1-2 (2006); Gao et al., J. Virol., 78: 6381-6388 (2004); Gao et al., Proc. Natl. Acad. Sci. USA, 99: 11854-11859 (2002); De et al., Mol. Ther., 13: 67-76 (2006); and Gao et al., Mol. Ther., 13: 77-87 (2006).

In one embodiment, the AAV vector is generated using an AAV that infects humans (e.g., AAV2). Alternatively, the AAV vector is generated using an AAV that infects non-human primates, such as, for example, the great apes (e.g., chimpanzees), Old World monkeys (e.g., macaques), and New World monkeys (e.g., marmosets). Preferably, the AAV vector is generated using an AAV that infects a non-human primate pseudotyped with an AAV that infects humans. Examples of such pseudotyped AAV vectors are disclosed in, e.g., Cearley et al., Molecular Therapy, 13: 528-537 (2006). In one embodiment, an AAV vector can be generated which comprises a capsid protein from an AAV that infects rhesus macaques pseudotyped with AAV2 inverted terminal repeats (ITRs). In a particularly preferred embodiment, the inventive AAV vector comprises a capsid protein from AAV10 (also referred to as "AAVrh.10"), which infects rhesus macaques pseudotyped with AAV2 ITRs (see, e.g., Watanabe et al., Gene Ther., 17(8): 1042-1051 (2010); and Mao et al., Hum. Gene Therapy, 22: 1525-1535 (2011)).

An AAV vector, as disclosed herein, comprises a nucleic acid sequence encoding an arginine-degrading enzyme polypeptide. "Nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides.

In some embodiments, a vector comprising a nucleic acid sequence encoding a DNAJB6-targeting antisense oligonucleotide (ASO) can be a plasmid, cosmid, yeast artificial chromosome (YAC), bacterial artificial chromosome (BAC), viral vector or bacteriophage. The vectors can provide for replication of a DNAJB6-targeting antisense oligonucleotide (ASO) nucleic acids, expression of a DNAJB6-targeting antisense oligonucleotide (ASO) or integration of a DNAJB6-targeting antisense oligonucleotide (ASO) into the chromosome of a host cell. The choice of vector is dependent on the desired purpose. Certain cloning vectors are useful for cloning, mutation and manipulation of the DNAJB6-targeting antisense oligonucleotide (ASO) encoding nucleic acid. Other vectors are useful for expression of a DNAJB6-targeting antisense oligonucleotide (ASO. The vector can also be chosen on the basis of the host cell, e.g., to facilitate expression in bacteria, mammalian cells, insect cells, fish cell (e.g., zebrafish) and/or amphibian cells. The choice of matching vector to host cell is apparent to one of skill in the art, and the types of host cells are discussed below. Many vectors or vector systems are available commercially, for example, the pET bacterial expression system (Invitrogen™, Carlsbad Calif.).

The vectors disclosed herein can be viral or non-viral vectors. For example, as discussed above the disclosed vectors can be viral vectors. There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain neurodegenerative diseases or disorders and cell populations by using the targeting characteristics of the carrier.

Vectors can include various components including, but not limited to, an origin of replication, one or more marker or selectable genes (e.g. GFP, neo), promoters, enhancers, terminators, poly-adenylation sequences, repressors or activators. Such elements are provided in the vector so as to be operably linked to the coding region of a DNAJB6-targeting antisense oligonucleotide (ASO)-encoding nucleic acid, thereby facilitating expression in a host cell of interest. Cloning and expression vectors can contain an origin of replication which allows the vector to replicate in the host cells. Vectors can also include a selectable marker, e.g., to confer a resistance to a drug or compliment deficiencies in growth. Examples of drug resistance markers include, but are not limited to, ampicillin, tetracycline, neomycin or methotrexate. Examples of other marker genes can be the fluorescent polypeptides such one of the members of the fluorescent family of proteins, for example, GFP, YFP, BFP, RFP etc. These markers can be contained on the same vector as the gene of interest or can be on separate vectors and co-transfected with the vector containing the gene of interest.

The vector can contain a promoter that is suitable for expression of the DNAJB6-targeting ASO in mammalian cells, which promoter can be operably linked to provide for inducible or constitutive expression of an arginine-degrading enzyme polypeptide. Exemplary inducible promoters include, for example, the metallothionine promoter or an ecdysone-responsive promoter. Exemplary constitutive promoters include, for ex-ample, the viral promoters from cytomegalovirus (CMV), Rous Sarcoma virus (RSV), Simian virus 40 (SV40), avian sarcoma virus, the beta-actin promoter and the heat-shock promoters. The promoter can be chosen for its tissue specificity. Certain promoters only express in certain tissues, and when it is desirable to express the polypeptide of interest only in a selected tissue, one of these promoters can be used. The choice of promoter will be apparent to one of skill in the art for the desired host cell system.

The vector encoding an arginine-degrading enzyme can be a viral vector. Examples of viral vectors include retroviral vectors, such as: adenovirus, simian virus 40 (SV40), cytomegalovirus (CMV), Moloney murine leukemia virus (Mo-MuLv), Rous Sar-coma Virus (RSV), lentivirus, herpesvirus, poxvirus and vaccinia virus. A viral vector can be used to facilitate expression in a target cell, e.g., for production of arginine-degrading enzyme or for use in therapy (e.g., to deliver an arginine-degrading enzyme to a subject by expression from the vector). Where used for therapy, arginine-degrading enzyme-encoding vectors (e.g, viral vectors), can be administered directly to the patient via an appropriate route or can be administered using an ex vivo strategy using subject cells (autologous) or allogeneic cells, which are suitable for administration to the patient to be treated.

As used herein, plasmid or viral vectors are agents that transport the disclosed nucleic acids, such as a nucleic acid sequence capable of encoding one or more of the disclosed peptides into the cell without degradation and include a promoter yielding expression of the gene in the cells into which it is delivered. In some embodiments the nucleic acid sequences disclosed herein are derived from any viral families which share the properties of these viruses which make them suitable for use as vectors. Retroviruses include Murine Maloney Leukemia virus, MMLV, and retroviruses that ex-press the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. The viral vectors may be formulated in pharmaceutical compositions as those described above Retroviral vectors, in general, are described by Verma, I. M., Retroviral vectors for gene transfer. In Microbiology, Amer. Soc. for Microbiology, pp. 229-232, Washington, (1985), which is hereby incorporated by reference in its entirety. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference in their entirety for their teaching of methods for using retroviral vectors for gene therapy.

Other useful systems include, for example, replicating and host-restricted non-replicating vaccinia virus vectors. In addition, the disclosed nucleic acid sequences can be delivered to a target cell in a non-nucleic acid based system. For example, the disclosed polynucleotides can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed expression vectors, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a peptide and a cationic liposome can be administered to the blood, to a target organ, or inhaled into the respiratory tract to target cells of the respiratory tract. For example, a composition comprising a peptide or nucleic acid sequence described herein and a cationic liposome can be administered to a subjects lung cells. Regarding liposomes, see, e.g., Brigham et al. Am. J. Resp. Cell. Mol. Biol. 1:95-100 (1989); Feigner et al. Proc. Natl. Acad. Sci USA 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

Exemplary host cells include bacteria, yeast, mammalian cells (e.g., human cells or cell lines), insect cells, and the like. Examples of bacterial host cells include *E. coli* and other bacteria which can find use in cloning, manipulation and production of arginine-degrading enzyme nucleic acids or the production of arginine-degrading enzyme poly-peptide. Examples of mammalian cells include, but are not limited to, Chinese hamster ovary (CHO) cells, HEK 293 cells, human cervical carcinoma cells (Hela), canine kidney cells (MDCK), human liver cells (HepG2), baby hamster kidney cells (BHK), and monkey kidney cells (CV1).

The invention includes methods for preparing pharmaceutical compositions for modulating the expression or activity of DNAJB6. Such methods comprise formulating a pharmaceutically acceptable carrier with an agent which modulates expression or activity of DNAJB6. Such compositions can further include additional active agents. Thus, the invention further includes methods for preparing a pharmaceutical composition by formulating a pharmaceutically acceptable carrier with an agent which modulates expression or activity of DNAJB6 and one or more additional active compounds.

An agent which modulates expression or activity may, for example, be a small molecule. For example, such small molecules include peptides, peptidomimetics, amino acids, amino acid analogs, polynucleotides, polynucleotide analogs, nucleotides, nucleotide analogs, organic or inorganic compounds (i.e., including hetero-organic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the knowledge of the ordinarily skilled artisan. The dose(s) of the small molecule will vary, for example, depending upon the identity, size, and condition of the subject or sample being treated, further depending upon the route by which the composition is to be administered, if applicable, and the effect which the practitioner desires the small molecule to have. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of DNAJB6, a physician, veterinarian, or researcher may, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention may be formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use may include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.), or phosphate buffered saline (PBS). In all cases, a composition may be sterile and may be fluid to the extent that easy syringeability exists. A composition may be stable under the conditions of manufacture and storage and may be preserved against the contaminating action of microorganisms such as bacteria and fungi. The carrier may be a solvent or dispersion medium containing, for example, water, ethanol, polyol (for example, glycerol, propylene glycol, and liquid polyetheylene glycol, and the like), and suitable mixtures thereof. The proper fluidity may be maintained, for example, by the use of a coating such as lecithin, by the maintenance of the required particle size in the case of dispersion, and by the use of surfactants. Prevention of the action of microorganisms may be achieved by various antibacterial and antifungal agents, for example, parabens, chlorobutanol, phenol, ascorbic acid, thimerosal, and the like. In many cases, it may be preferable to include isotonic agents, for example, sugars, polyalcohols such as mannitol, sorbitol, or sodium chloride, in the composition. Prolonged absorption of the injectable compositions may be brought about by including in the composition an agent which delays absorption, for example, aluminum monostearate and gelatin.

Sterile injectable solutions may be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional de-sired ingredient from a previously sterile-filtered solution thereof.

Oral compositions generally may include an inert diluent or an edible carrier. Oral compositions may be enclosed in gelatin capsules or compressed into tablets. For the purpose of oral therapeutic administration, the active compound may be incorporated with excipients and used in the form of tablets, troches, or capsules. Oral compositions may also be prepared using a fluid carrier for use as a mouthwash, wherein the compound in the fluid carrier is applied orally and swished and expectorated or swallowed. Pharmaceutically compatible binding agents and/or adjuvant materials may be included as part of the composition. The tablets, pills, capsules, troches, and the like, may contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressured container or dispenser which contains a suitable propellant, e.g., a gas such as carbon dioxide, or a nebulizer.

Systemic administration may also be by transmucosal or transdermal means. For transmucosal or transdermal administration, penetrants appropriate to the barrier to be permeated are used in the formulation. Such penetrants are generally known in the art, and may include, for example, for transmucosal administration, detergents, bile salts, and fusidic acid derivatives. Transmucosal administration may be accomplished through the use of nasal sprays or suppositories. For transdermal administration, the active compounds are formulated into ointments, salves, gels, or creams as generally known in the art. The compounds may also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, and polylactic acid. Methods for preparation of such formulations will be apparent to those skilled in the art. These may be prepared according to methods known to those skilled in the art, for example, as described in U.S. Pat. No. 4,522,811.

As used herein, the term "biological sample" refers to a sample obtained from a subject. Any biological sample comprising a DNAJB6 is suitable. Non-limiting examples include tissue biopsy, blood, plasma, serum, urine, cerebrospinal fluid (CSF) and interstitial fluid (ISF). In a specific embodiment, the biological sample comprises motor neurons. The sample may be used "as is", the cellular components may be isolated from the sample, or a protein fraction may be isolated from the sample using standard techniques.

As will be appreciated by a skilled artisan, the method of collecting a biological sample can and will vary depending upon the nature of the biological sample and the type of analysis to be performed. Any of a variety of methods generally known in the art may be utilized to collect a biological sample. Generally speaking, the method preferably maintains the integrity of the sample such that the DNAJB6 can be accurately detected and the amount measured according to the invention.

Methods for assessing an amount of nucleic acid expression in cells are well known in the art, and all suitable methods for assessing an amount of nucleic acid expression known to one of skill in the art are contemplated within the scope of the invention. The term "amount of nucleic acid expression" or "level of nucleic acid expression" as used herein refers to a measurable level of expression of the nucleic acids, such as, without limitation, the level of RNA transcript expressed or a specific variant or other portion of the RNA. The term "nucleic acid" includes DNA and RNA and can be either double stranded or single stranded. Non-limiting examples of suitable methods to assess an amount of nucleic acid expression may include arrays, such as microarrays, PCR, such as RT-PCR (including quantitative RT-PCR), nuclease protection assays and Northern blot analyses. In a specific embodiment, determining the amount of a RNA comprises, in part, measuring the level of RNA expression.

In one embodiment, the amount of nucleic acid expression may be determined by using an array, such as a microarray. Methods of using a nucleic acid microarray are well and widely known in the art. For example, a nucleic acid probe that is complementary or hybridizable to an expression product of a target gene may be used in the array. The term "hybridize" or "hybridizable" refers to the sequence specific non-covalent binding interaction with a complementary nucleic acid. In a preferred embodiment, the hybridization is under high stringency conditions. Appropriate stringency conditions which promote hybridization are known to those skilled in the art, or can be found in Current Protocols in Molecular Biology, John Wiley & Sons, N.Y. (1989), 6.3.1 6.3.6. The term "probe" as used herein refers to a nucleic acid sequence that will hybridize to a nucleic acid target sequence. In one example, the probe hybridizes to an RNA product of the nucleic acid or a nucleic acid sequence complementary thereof. The length of probe depends on the hybridization conditions and the sequences of the probe and nucleic acid target sequence. In one embodiment, the probe is at least 8, 10, 15, 20, 25, 50, 75, 100, 150, 200, 250, 400, 500 or more nucleotides in length.

In another embodiment, the amount of nucleic acid expression may be determined using PCR. A nucleic acid may be amplified using cDNA, mRNA or genomic DNA as a template and appropriate oligonucleotide primers according to standard PCR amplification techniques. Methods of PCR are well and widely known in the art, and may include quantitative PCR, semi-quantitative PCR, multiplex PCR, or any combination thereof. Specifically, the amount of nucleic expression may be determined using quantitative RT-PCR. Methods of performing quantitative RT-PCR are common in the art. In such an embodiment, the primers used for quantitative RT-PCR may comprise a forward and reverse primer for a target gene. The term "primer" as used herein refers to a nucleic acid sequence, whether occurring naturally as in a purified restriction digest or produced synthetically, which is capable of acting as a point of synthesis when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less or more. The factors involved in determining the appropriate length of primer are readily known to one of ordinary skill in the art.

The amount of nucleic acid expression may be measured by measuring an entire RNA transcript for a nucleic acid sequence, or measuring a portion of the RNA transcript for a nucleic acid sequence. For instance, if a nucleic acid array is utilized to measure the amount of RNA expression, the array may comprise a probe for a portion of the RNA of the nucleic acid sequence of interest, or the array may comprise a probe for the full RNA of the nucleic acid sequence of interest. Similarly, in a PCR reaction, the primers may be designed to amplify the entire cDNA sequence of the nucleic acid sequence of interest, or a portion of the cDNA sequence. One of skill in the art will recognize that there is more than one set of primers that may be used to amplify either the entire cDNA or a portion of the cDNA for a nucleic acid sequence of interest. Methods of designing primers are known in the art. Methods of extracting RNA from a biological sample are known in the art.

The level of expression may or may not be normalized to the level of a control nucleic acid. Such a control nucleic acid should not specifically hybridize with an ASO nucleotide sequence of the invention. This allows comparisons between assays that are performed on different occasions. In certain embodiments, the level of expression is normalized to a control nucleic acid.

The step of quantifying DNAJB6 comprises performing liquid chromatography-mass spectrometry (LC-MS) with a sample. Tandem mass spectrometry may be used to improve resolution, as is known in the art, or technology may improve to achieve the resolution of tandem mass spectrometry with a single mass analyzer. Suitable types of mass spectrometers are known in the art. These include, but are not limited to, quadrupole, time-of-flight, ion trap and Orbitrap, as well as hybrid mass spectrometers that combine different types of mass analyzers into one architecture (e.g., Orbitrap Fusion™ Tribrid™ Mass Spectrometer, Orbitrap Fusion™ Lumos™ Mass Spectrometer, Orbitrap Tribrid™ Eclipse™ Mass Spectrometer, Q Exactive Mass Spectrometer, each from ThermoFisher Scientific). In an exemplary embodiment, an LC-MS system may comprise a mass spectrometer selected from Orbitrap Fusion™ Tribrid™ Mass Spectrometer, Orbitrap Fusion™ Lumos™ Mass Spectrometer, Orbitrap Tribrid™ Eclipse™ Mass Spectrometer, or a mass spectrometer with similar or improved ion-focusing and ion-transparency at the quadrupole. Suitable mass spectrometry protocols may be developed by optimizing the number of ions collected prior to analysis (e.g., AGC setting using an orbitrap) and/or injection time. In an exemplary embodiment, a mass spectrometry protocol outlined in the Examples is used.

In another embodiment, DNAJB6 can be measured and quantified by immunoassay. In a specific embodiment, DNAJB6 are detected and quantified using an ELISA.

Methods for assessing an amount of protein expression using epitope binding agent-based methods are known in the art and all suitable methods for assessing an amount of protein known to one of skill in the art are contemplated within the scope of the present disclosure.

Thus, in some embodiments, the method to assess an amount of tau protein is an epitope binding agent-based method. In general, an epitope binding agent-based method of assessing an amount of protein expression comprises contacting a sample comprising a polypeptide with an epitope binding agent specific for the polypeptide under conditions effective to allow for formation of a complex between the epitope binding agent and the polypeptide. Epitope binding agent-based method may occur in solution, or the epitope binding agent or sample may be immobilized on a solid surface. Non-limiting examples of suitable surfaces include microtiter plates, test tubes, beads, resins, and other polymers.

An epitope binding agent may be attached to the substrate in a wide variety of ways, as will be appreciated by those in the art. The epitope binding agent may either be synthesized first, with subsequent attachment to the substrate, or may be directly synthesized on the substrate. The substrate and the epitope binding agent may be derivatized with chemical functional groups for subsequent attachment of the two. For example, the substrate may be derivatized with a chemical functional group including, but not limited to, amino groups, carboxyl groups, oxo groups or thiol groups. Using these functional groups, the epitope binding agent may be attached directly using the functional groups or indirectly using linkers.

The epitope binding agent may also be attached to the substrate non-covalently. For example, a biotinylated epitope binding agent may be prepared, which may bind to surfaces covalently coated with streptavidin, resulting in attachment. Alternatively, an epitope binding agent may be synthesized on the surface using techniques such as photopolymerization and photolithography. Additional methods of attaching epitope binding agents to solid surfaces and methods of synthesizing biomolecules on substrates are well known in the art, i.e. VLSIPS technology from Affymetrix (e.g., see U.S. Pat. No. 6,566,495, and Rockett and Dix, Xenobiotica 30(2):155-177, both of which are hereby incorporated by reference in their entirety).

Contacting the sample with an epitope binding agent under effective conditions for a period of time sufficient to allow formation of a complex generally involves adding the epitope binding agent composition to the sample and incubating the mixture for a period of time long enough for the epitope binding agent to bind to any antigen pre-sent. After this time, the complex will be washed and the complex may be detected by any method well known in the art. Methods of detecting the epitope binding agent-polypeptide complex are generally based on the detection of a label or marker. The term "label", as used herein, refers to any substance attached to an epitope binding agent, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, stretpavidin, protein A, protein G, antibodies or fragments thereof, polyhistidine, $Ni^{2+}$, Flag tags, myc tags, heavy metals, and enzymes (including alkaline phosphatase, peroxidase, and luciferase). Methods of detecting an epitope binding agent-polypeptide complex based on the detection of a label or marker are well known in the art.

In some embodiments, an epitope binding agent-based method is an immunoassay. Immunoassays can be run in a number of different formats. Generally speaking, immunoassays can be divided into two categories: competitive immmunoassays and non-competitive immunoassays. In a competitive immunoassay, an unlabeled analyte in a sample competes with labeled analyte to bind an antibody. Unbound analyte is washed away and the bound analyte is measured. In a noncompetitive immunoassay, the antibody is labeled, not the analyte. Non-competitive immunoassays may use one antibody (e.g. the capture antibody is labeled) or more than one antibody (e.g. at least one capture antibody which is unlabeled and at least one "capping" or detection antibody which is labeled.) Suitable labels are described above.

In an embodiment, the epitope binding agent method is an immunoassay. In another embodiment, the epitope binding agent method is selected from the group consisting of an enzyme linked immunoassay (ELISA), a fluorescence based assay, a dissociation enhanced lanthanide fluoroimmunoassay (DELFIA), a radiometric assay, a multiplex immunoassay, and a cytometric bead assay (CBA). In some embodiments, the epitope binding agent-based method is an enzyme linked immunoassay (ELISA). In other embodiments, the epitope binding agent-based method is a radioimmunoassay. In still other embodiments, the epitope binding agent-based method is an immunoblot or Western blot. In alternative embodiments, the epitope binding agent-based method is an array. In another embodiment, the epitope binding agent-based method is flow cytometry. In different embodiments, the epitope binding agent-based method is immunohistochemistry (IHC). IHC uses an antibody to detect and quantify antigens in intact tissue samples. The tissue samples may be fresh-frozen and/or formalin-fixed, paraffin-embedded (or plastic-embedded) tissue blocks prepared for study by IHC. Methods of preparing tissue block for study by IHC, as well as methods of performing IHC are well known in the art.

In certain embodiments, to classify the amount of DNAJB6 as increased in a biological sample, the amount of DNAJB6 in the biological sample compared to the reference value is increased at least 2-fold. For example, the amount of miRNA in the sample compared to the reference value is increased at least 2-fold, at least 5-fold, at least 10-fold, at least 15-fold, at least 20-fold, at least 25-fold, at least 30-fold, at least 35-fold, at least 40-fold, at least 45-fold, at least 50-fold, at least 100-fold, at least 200-fold, at least 300-fold, at least 400-fold, at least 500-fold, at least 1000-fold, at least 5000-fold, or at least 10000-fold.

In certain embodiments, to classify the amount of DNAJB6 as decreased in a biological sample, the amount of DNAJB6 in the biological sample compared to the reference value is decreased at least 2-fold. For example, the amount of miRNA in the sample compared to the reference value is decreased at least 2-fold, at least 5-fold, at least 10-fold, at least 15-fold, at least 20-fold, at least 25-fold, at least 30-fold, at least 35-fold, at least 40-fold, at least 45-fold, at least 50-fold, at least 100-fold, at least 200-fold, at least 300-fold, at least 400-fold, at least 500-fold, at least 1000-fold, at least 5000-fold, or at least 10000-fold.

In another embodiment, the increase or decrease in the amount of miRNA is measured using p-value. For instance, when using p-value, a DBAJB6 is identified as being differentially expressed between a biological sample and a reference value when the p-value is less than 0.1, preferably less than 0.05, more preferably less than 0.01, even more preferably less than 0.005, the most preferably less than 0.001.

According to the disclosure, the compositions described above are useful to treat a subject having a DNAJB6-related myopathies (e.g., autosomal dominant limb girdle muscular dystrophy type 1D (LGMD1D). The treatment modality may be altered if ineffectiveness of treatment or progression of DNAJB6-related myopathy is detected. The term "treatment" or "therapy" as used herein means any treatment suitable for the treatment. Treatment may consist of standard treatments for a DNAJB6-related myopathy. Non-limiting examples of standard treatment can include Riluzole (Rilutek), Tizanidine (Zanaflex), Baclofen, quinine, hyoscine hydrobromide skin patch, NSAIDs, gabapentin, physical therapy, acupuncture, immunotherapy, gene transfer therapy, stem cell and progenitor cell based cellular replacement therapy, antisense oligonucleotide therapy, antioxidant therapy, antidepressant therapy, antibody therapy, autophagy control therapy, drug therapy (small-molecule inhibitor of kynurenine 3-monooxygenase JM6), and any therapeutic agent known in the art or yet to be discovered. Still further, treatment may be as described below or with an agent as described in Section I.

Additional therapeutic agents may include those used in immunotherapy, gene transfer therapy, stem cell and progenitor cell based cellular replacement therapy, anti-sense oligonucleotide therapy, antioxidant therapy, antidepressant therapy, antibody therapy, autophagy control therapy, drug therapy (small-molecule inhibitor of kynurenine 3-monooxygenase JM6), and any therapeutic agent known in the art or yet to be discovered.

A DNAJB6 modulating agent of the invention may be administered to a subject by several different means. For instance, compositions may generally be administered in dosage unit formulations containing conventional nontoxic pharmaceutically acceptable carriers, adjuvants, and vehicles as desired.

Methods of administration include any method known in the art or yet to be discovered. Exemplary administration methods include intravenous, intraocular, intratracheal, intratumoral, oral, rectal, topical, intramuscular, intraarterial, intrahepatic, intrathoracic, intrathecal, intracranial, intraperitoneal, intrapancreatic, intrapulmonary, or subcutaneously. A composition of the invention may also be administered directly by infusion into central nervous system fluid. One skilled in the art will appreciate that the route of administration and method of administration depend upon the intended use of the compositions, the location of the target area, and the condition being treated, in addition to other factors known in the art such as subject health, age, and physiological status.

In a preferred embodiment, the oligonucleotide may be administered parenterally. The term "parenteral" as used herein describes administration into the body via a route other than the mouth, especially via infusion, injection, or implantation, and includes intradermal, subcutaneous, transdermal implant, intracavernous, intravitreal, intraarticular or intrasynovial injection, transscleral, intracerebral, intrathecal, epidural, intravenous, intracardiac, intramuscular, intraosseous, intraperitoneal, intravenous, intrasternal injection, or nanocell injection. Formulation of pharmaceutical compositions is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

In some embodiments, a DNAJB6 modulating agent of the invention is ad-ministered parenterally. When DNAJB6 modulating agent is administered parenterally, delivery methods are preferably those that are effective to circumvent the blood-brain barrier, and are effective to deliver agents to the central nervous system. For ex-ample, delivery methods may include the use of nanoparticles. The particles may be of any suitable structure, such as unilamellar or plurilamellar, so long as the antisense oligonucleotide is contained therein. Positively charged lipids such as N-[1-(2,3-dioleoyloxi)propyl]-N, N,N-trimethyl-amoniummethylsulfate, or "DOTAP," are particularly preferred for such particles and vesicles. The preparation of such lipid particles is well known in the art. See, e.g., U.S. Pat. No. 4,880,635 to Janoff et al.; U.S. Pat. No. 4,906,477 to Kurono et al.; U.S. Pat. No.

4,911,928 to Wallach; U.S. Pat. No. 4,917,951 to Wallach; U.S. Pat. No. 4,920,016 to Allen et al.; U.S. Pat. No. 4,921,757 to Wheatley et al.; etc.

In another preferred embodiment, DNAJB6 modulating agent is administered by continuous infusion. Non-limiting examples of methods that may be used to deliver a DNAJB6 modulating agent by continuous infusion may include pumps, wafers, gels, foams and fibrin clots. In a preferred embodiment, DNAJB6 modulating agent is delivered by continuous infusion using an osmotic pump. An osmotic minipump contains a high osmolality chamber that surrounds a flexible, yet impermeable, reservoir filled with the targeted delivery composition containing vehicle. Subsequent to the subcutaneous implantation of this minipump, extracellular fluid enters through an outer semipermeable membrane into the high osmolality chamber, thereby compressing the reservoir to release the targeted delivery composition at a controlled, predetermined rate. The targeted delivery composition, released from the pump, may be directed via a catheter to a stereotaxically placed cannula for infusion into the cerebroventricular space.

Compositions of the invention are typically administered to a subject in an amount sufficient to provide a benefit to the subject. This amount is defined as a "therapeutically effective amount." A therapeutically effective amount may be determined by the efficacy or potency of the particular composition, the DNAJB6-related myopathy being treated, the duration or frequency of administration, the method of administration, and the size and condition of the subject, including that subject's particular treatment response. A therapeutically effective amount may be determined using methods known in the art, and may be determined experimentally, derived from therapeutically effective amounts determined in model animals such as the mouse, or a combination thereof. Additionally, the route of administration may be considered when determining the therapeutically effective amount. In determining the therapeutically effective amounts, one skilled in the art may also consider the existence, nature, and extent of any adverse effects that accompany the administration of a particular compound in a particular subject.

In some embodiments, when a DNAJB6 modulating agent is administered to the subject in an amount of about 0.1, 0.2, 0.3, 0.4, 0.5, 1, 1.5, 2, 2.5, 3, 3.5, 4, 4.5, 5, 6.5, 7, 7.5, 8, 8.5, 9, 9.5, 10, 10.5, 11, 11.5, 12, 12.5, 13, 13.5, 14, 14.5, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or about 100 µg/day or more.

One of skill in the art will also recognize that the duration of the administration by continuous infusion can and will vary, and will depend in part on the subject, the neurodegenerative disease, and the severity, progression and improvement of the condition of the subject, and may be determined experimentally.

When a DNAJB6 modulating agent is an antisense oligonucleotide, molecules of the invention are typically administered to a subject or generated in situ such that they hybridize with or bind to DNAJB6 RNA inhibiting the respective biological activity of DNAJB6. The hybridization may be by conventional nucleotide complementarity to form a stable duplex, or, for example, in the case of an antisense nucleic acid molecule which binds to DNA duplexes, through specific interactions in the major groove of the double helix. An antisense nucleic acid molecule of the invention may be administered by direct injection at a tissue site. Alternatively, antisense nucleic acid molecules may be modified to target selected cells and then administered systemically. For example, for systemic administration, antisense molecules may be modified such that they specifically bind to receptors or antigens expressed on a selected cell surface, e.g., by linking the antisense nucleic acid molecules to peptides or antibodies which bind to cell surface receptors or antigens. The antisense nucleic acid molecules may also be delivered by direct infusion into a subject. The antisense nucleic acid molecules may also be delivered to cells using gene therapy vectors known in the art. To achieve sufficient intracellular concentrations of the antisense molecules, vectors in which the antisense nucleic acid molecule is placed under the control of a strong pol II or pol III promoter are preferred.

As used herein, "subject" may refer to a living organism having a central nervous system. In particular, subjects may include, but are not limited to, human subjects or patients and companion animals. Exemplary companion animals may include domesticated mammals (e.g., dogs, cats, horses), mammals with significant commercial value (e.g., dairy cows, beef cattle, sporting animals), mammals with significant scientific value (e.g., captive or free specimens of endangered species), or mammals which otherwise have value. Suitable subjects may also include: mice, rats, dogs, cats, ungulates such as cattle, swine, sheep, horses, and goats, lagomorphs such as rabbits and hares, other rodents, and primates such as monkeys, chimps, and apes. In some preferred embodiments, a subject is a human. In other preferred embodiments, a subject is a rat. In yet other preferred embodiments, a subject is a mouse. Subjects may be of any age including newborn, adolescent, adult, middle age, or elderly.

Also provided is a process of treating, preventing, or reversing a neuromuscular disease, disorder, or condition in a subject in need of administration of a therapeutically effective amount of a gene-targeting antisense oligonucleotide (ASO) (e.g., designed to reduce or eliminate pathogenic isoform transcripts), so as to reduce or eliminate expression of pathogenic isoforms associated with a neuromuscular disease, disorder, or condition.

Methods described herein are generally performed on a subject in need thereof. A subject in need of the therapeutic methods described herein can be a subject having, diagnosed with, suspected of having, or at risk for developing a neuromuscular disease, disorder, or condition. A determination of the need for treatment will typically be assessed by a history, physical exam, or diagnostic tests consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and humans or chickens. For example, the subject can be a human subject.

Generally, a safe and effective amount of a gene-targeting ASO is, for example, an amount that would cause the desired therapeutic effect in a subject while minimizing undesired side effects. In various embodiments, an effective amount of a gene-targeting ASO described herein can substantially reduce or inhibit expression of pathogenic isoforms, slow the progress of a neuromuscular disease, disorder, or condition, or limit the development of a neuromuscular disease, disorder, or condition.

According to the methods described herein, administration can be parenteral, pulmonary, oral, topical, intradermal, intramuscular, intraperitoneal, intravenous, intratumoral, intrathecal, intracranial, intracerebroventricular, subcutaneous, intranasal, epidural, ophthalmic, buccal, or rectal administration.

When used in the treatments described herein, a therapeutically effective amount of a gene-targeting ASO can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to reduce or inhibit expression of pathogenic isoforms, slow the progress of a neuromuscular disease, disorder, or condition, or limit the development of a neuromuscular disease, disorder, or condition.

The amount of a composition described herein that can be combined with a pharmaceutically acceptable carrier to produce a single dosage form will vary depending upon the subject or host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing, reversing, or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of a gene-targeting ASO can occur as a single event or over a time course of treatment. For example, a gene-targeting ASO can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for a neuromuscular disease, disorder, or condition.

A gene-targeting ASO can be administered simultaneously or sequentially with another agent, such as an antibiotic, an anti-inflammatory, or another agent. For example, a gene-targeting ASO can be administered simultaneously with another agent, such as an antibiotic or an anti-inflammatory. Simultaneous administration can occur through administration of separate compositions, each containing one or more of a gene-targeting ASO, an antibiotic, an anti-inflammatory, or another agent. Simultaneous administration can occur through administration of one composition containing two or more of a gene-targeting ASO, an antibiotic, an anti-inflammatory, or another agent. A gene-targeting ASO can be administered sequentially with an antibiotic, an anti-inflammatory, or another agent. For example, a gene-targeting ASO can be administered before or after administration of an antibiotic, an anti-inflammatory, or another agent.

A subject may be at risk for developing a DNAJB6-related myopathy. As such, in some embodiments, treating a DNAJB6-related myopathy prevents a disorder from developing in a subject at risk of developing or such that a disease or disorder is prevented, or delayed in its progression.

A subject may also be diagnosed as having a DNAJB6-related myopathy. Treating a subject using a method of the invention may extend the survival of the subject. Alternatively, treating a subject using a method of the invention may extend the disease duration of the subject.

In some embodiments, treating a subject extends the survival of the subject. A method of the invention may extend the survival of a subject by days, weeks, months, or years, when compared to the survival of a subject that was not treated using a method of the invention. As will be recognized by individuals skilled in the art, the number of days, months, or years that a method of the invention may extend the survival of a subject can and will vary depending on the subject, the DNAJB6-related myopathy, and the condition of the subject when treatment was initiated among other factors.

In other embodiments, treating a subject extends the disease duration of a subject. As used herein, the term "disease duration" is used to describe the length of time between onset of symptoms and death caused by the disease.

A method of the invention may extend the disease duration of a subject by days, weeks, months, or years, when compared to the survival of the subject that was not treated using a method of the invention. The number of days, months, or years that a method of the invention may extend the disease duration of a subject can and will vary depending on the subject, the DNAJB6-related myopathy, and the condition of the subject when treatment was initiated among other factors.

In still other aspects, the present invention provides articles of manufacture and kits containing materials useful for treating the conditions described herein. The article of manufacture may include a container of a composition as described herein with a label. Suitable containers include, for example, bottles, vials, and test tubes. The containers may be formed from a variety of materials such as glass or plastic. The container holds a composition having an active agent which is effective for treating, for example, conditions that benefit from activity and/or expression. The active agent is at least one DNAJB6 modulating agent as disclosed herein and may further include additional bioactive agents known in the art for treating the specific condition. The label on the container may indicate that the composition is useful for treating specific conditions and may also indicate directions for administration.

Definitions

When introducing elements of the present disclosure or the preferred aspects(s) thereof, the articles "a," "an," "the," and "said" are intended to mean that there are one or more of the elements. The terms "comprising," "including," and "having" are intended to be inclusive and mean that there may be additional elements other than the listed elements.

As used herein, the following definitions shall apply unless otherwise indicated. For purposes of this invention, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry," Thomas Sorrell, University Science Books, Sausalito: 1999, and "March's Advanced Organic Chemistry," 5$^{th}$ Ed., Smith, M. B. and March, J., eds. John Wiley & Sons, New York: 2001, the entire contents of which are hereby incorporated by reference.

The term "mmol", as used herein, is intended to mean millimole. The term "equiv", as used herein, is intended to mean equivalent. The term "mL", as used herein, is intended to mean milliliter. The term "g", as used herein, is intended to mean gram. The term "kg", as used herein, is intended to mean kilogram. The term "µg", as used herein, is intended to mean micrograms. The term "h", as used herein, is intended to mean hour. The term "min", as used herein, is intended to mean minute. The term "M", as used herein, is intended to mean molar. The term "µL", as used herein, is intended to mean microliter. The term "µM", as used herein, is intended to mean micromolar. The term "nM", as used herein, is intended to mean nanomolar. The term "N", as used herein, is intended to mean normal. The term "amu", as used herein, is intended to mean atomic mass unit. The term "° C.", as used herein, is intended to mean degree Celsius. The term "wt/wt", as used herein, is intended to mean weight/weight. The term "v/v", as used herein, is intended to mean volume/volume. The term "MS", as used herein, is intended to mean mass spectroscopy. The term "HPLC", as used herein, is intended to mean high performance liquid chromatograph. The term "RT", as used herein, is intended to mean room temperature. The term "e.g.", as used herein, is intended to mean example. The term "N/A", as used herein, is intended to mean not tested.

As used herein, the expression "pharmaceutically acceptable salt" refers to pharmaceutically acceptable organic or inorganic salts of a compound of the invention. Preferred salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, or pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counterions. Hence, a pharmaceutically acceptable salt can have one or more charged atoms and/or one or more counterion. As used herein, the expression "pharmaceutically acceptable solvate" refers to an association of one or more solvent molecules and a compound of the invention. Examples of solvents that form pharmaceutically acceptable solvates include, but are not limited to, water, isopropanol, ethanol, methanol, DMSO, ethyl acetate, acetic acid, and ethanolamine. As used herein, the expression "pharmaceutically acceptable hydrate" refers to a compound of the invention, or a salt thereof, that further includes a stoichiometric or non-stoichiometric amount of water bound by non-covalent intermolecular forces.

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

Expression vector, expression construct, plasmid, or recombinant DNA construct is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the start site of transcription, such as, in the case of a polymerase II type promoter, a TATA element. A promoter can optionally include distal enhancer or repressor elements, which can be located as much as several thousand base pairs from the start site of transcription.

A "transcribable nucleic acid molecule" as used herein refers to any nucleic acid molecule capable of being transcribed into a RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present disclosure, conventional compositions and methods for preparing and using constructs and host cells are well known to one skilled in the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754).

The "transcription start site" or "initiation site" is the position surrounding the first nucleotide that is part of the transcribed sequence, which is also defined as position +1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) are denominated negative.

A nucleic acid sequence or amino acid sequence (e.g., DNA, RNA, a genetic sequence, polynucleotide, oligonucleotide, primer, protein, polypeptide, peptide) can have about 80%; about 81%; about 82%; about 83%; about 84%; about 85%; about 86%; about 87%; about 88%; about 89%; about 90%; about 91%; about 92%; about 93%; about 94%; about 95%; about 96%; about 97%; about 98%; or about 99% sequence identity to a reference sequence or a naturally occurring sequence or contain at least one substitution modification to the reference sequence or naturally occurring sequence. Recitation of each of these discrete values is understood to include ranges between each value.

A nucleic acid sequence or an amino acid sequence can be operably linked to a heterologous promoter.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A constructs of the present disclosure can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule which can play an important role in translation initiation and can also be a genetic component in an expression construct. These additional upstream and downstream regulatory nucleic acid molecules may be derived from a source that is native or heterologous with respect to the other elements present on the promoter construct.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a bacterium, cyanobacterium, animal or a plant into which a heterologous nucleic acid molecule has been introduced. The nucleic acid molecule can be stably integrated into the genome as generally known in the art and disclosed (Sambrook 1989; Innis 1995; Gelfand 1995; Innis & Gelfand 1999). Known methods of PCR include, but are not limited to, methods using paired primers, nested primers, single specific primers, degenerate primers, gene-specific primers, vector-specific primers, partially mismatched primers, and the like. The term "untransformed" refers to normal cells that have not been through the transformation process.

"Wild-type" refers to a virus or organism found in nature without any known mutation.

Design, generation, and testing of the variant nucleotides, and their encoded polypeptides, having the above required percent identities and retaining a required activity of the expressed protein is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide and/or polypeptide variants having, for example, at least 95-99% identity to the reference sequence described herein and screen such for desired phenotypes according to methods routine in the art.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Generally, conservative substitutions can be made at any position so long as the required activity is retained. So-called conservative exchanges can be carried out in which the amino acid which is replaced has a similar property as the original amino acid, for example the exchange of Glu by Asp, Gln by Asn, Val by Ile, Leu by Ile, and Ser by Thr. For example, amino acids with similar properties can be Aliphatic amino acids (e.g., Glycine, Alanine, Valine, Leucine, Isoleucine); Hydroxyl or sulfur/selenium-containing amino acids (e.g., Serine, Cysteine, Selenocysteine, Threonine, Methionine); Cyclic amino acids (e.g., Proline); Aromatic amino acids (e.g., Phenylalanine, Tyrosine, Tryptophan); Basic amino acids (e.g., Histidine, Lysine, Arginine); or Acidic and their Amide (e.g., Aspartate, Glutamate, Asparagine, Glutamine). Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. Amino acid sequence can be modulated with the help of art-known computer simulation programs that can produce a polypeptide with, for example, improved activity or altered regulation. On the basis of this artificially generated polypeptide sequences, a corresponding nucleic acid molecule coding for such a modulated polypeptide can be synthesized in-vitro using the specific codon-usage of the desired host cell.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature (Tm) of a DNA duplex between the two sequences. If a particular duplex has a melting temperature lower than 65° C. in the salt conditions of a 6×SSC, then the two sequences will not hybridize. On the other hand, if the melting temperature is above 65□C in the same salt conditions, then the sequences will hybridize. In general, the melting temperature for any hybridized DNA:DNA sequence can be determined using the following formula: Tm=81.5° C.+16.6(log10[Na+])+0.41(fraction G/C content)−0.63(% formamide)−(600/l). Furthermore, the Tm of a DNA:DNA hybrid is decreased by 1-1.5° C. for every 1% decrease in nucleotide identity (see e.g., Sambrook and Russel, 2006).

Host cells can be transformed using a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Exemplary nucleic acids which may be introduced to a host cell include, for example, DNA sequences or genes from another species, or even genes or sequences which originate with or are present in the same species, but are incorporated into recipient cells by genetic engineering methods. The term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the cell, DNA from another individual of the same type of organism, DNA from a different organism, or a DNA generated externally, such as a DNA sequence containing an antisense message of a gene, or a DNA sequence encoding a synthetic or modified version of a gene.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Methods of down-regulation or silencing genes are known in the art. For example, expressed protein activity can be down-regulated or eliminated using antisense oligonucleotides, protein aptamers, nucleotide aptamers, and RNA interference (RNAi) (e.g., small interfering RNAs (siRNA), short hairpin RNA (shRNA), and micro RNAs (miRNA) (see e.g., Fanning and Symonds (2006) Handb Exp Pharmacol. 173, 289-303G, describing hammerhead ribozymes and small hairpin RNA; Helene, C., et al. (1992) Ann. N.Y. Acad. Sci. 660, 27-36; Maher (1992) Bioassays 14(12): 807-15, describing targeting deoxyribonucleotide sequences; Lee et al. (2006) Curr Opin Chem Biol. 10, 1-8, describing aptamers; Reynolds et al. (2004) Nature Biotechnology 22(3), 326-330, describing RNAi; Pushparaj and Melendez (2006) Clinical and Experimental Pharmacology and Physiology 33(5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, Tex.; Sigma Aldrich, Mo.; Invitrogen). Several siRNA molecule design programs using a variety of algorithms are known to the art (see e.g., Cenix algorithm, Ambion; BLOCK-iT™ RNAi Designer, Invitrogen; siRNA Whitehead Institute Design Tools, Bioinofrmatics & Research Computing). Traits influential in defining optimal siRNA sequences include G/C content at the termini of the siRNAs, Tm of specific internal domains of the siRNA, siRNA length, position of the target sequence within the CDS (coding region), and nucleotide content of the 3' overhangs.

Specific embodiments disclosed herein may be further limited in the claims using "consisting of" or "consisting essentially of" language, rather than "comprising". When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

As various changes could be made in the above-described materials and methods without departing from the scope of the invention, it is intended that all matter contained in the above description and in the examples given below, shall be interpreted as illustrative and not in a limiting sense.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: DNAJB6 Knockdown Strategies for LGMD-D1

An era where gene-based therapies for disabling and life-threatening neuromuscular disorders are becoming a reality. Currently, the limb girdle muscular dystrophy (LGMD) gene therapy field is focused almost entirely on recessively inherited disorders. The gene replacement strategies commonly employed are not translatable to dominantly inherited LGMDs, leaving them far behind in the path towards a cure. Therapies for dominant LGMDs require special consideration given their complex mechanisms. Recent, work has discovered mutations in DNAJB6 which cause LGMDD1, a disabling, adult onset, dominantly inherited, myopathy. There is a growing urgency for a treatment. Genetic discovery efforts are identifying more and more patients, and patient advocacy groups are growing. In fact, since its discovery in 2012, mutations in DNAJB6 are now the most common cause of dominantly inherited LGMD.

Figure 1B:
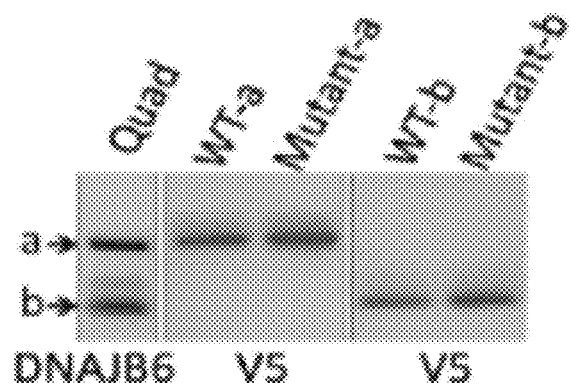
FIG. 1B shows western blot of skeletal muscle lysates from control (quad) or transgenic mice overexpressing V5 tagged WT or mutant DNAJB6a or DNAJB6b.
Figure 1C:
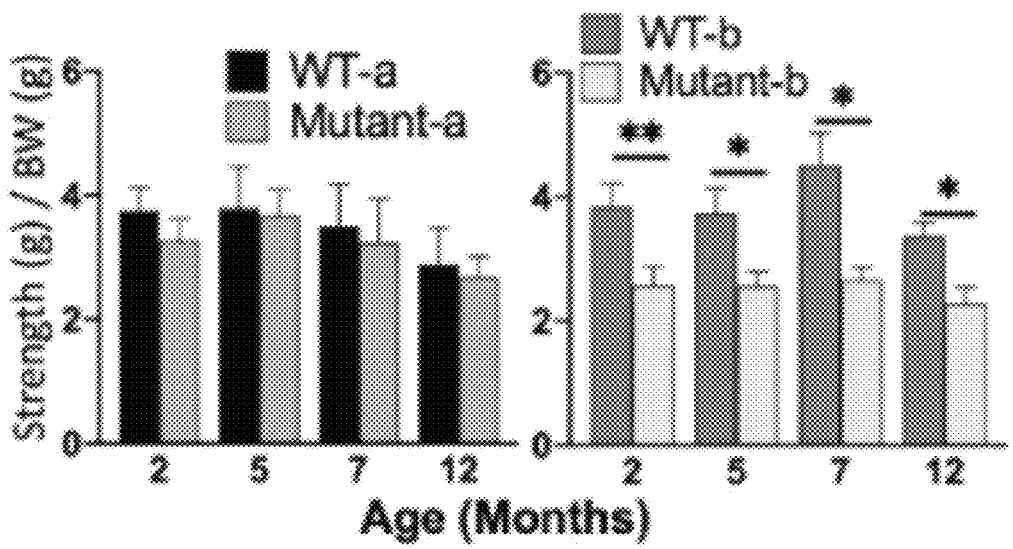
FIG. 1C shows only mutant DNAJB6b mice develop weakness. **P<0.000001. *P<0.00001
Figure 2A:
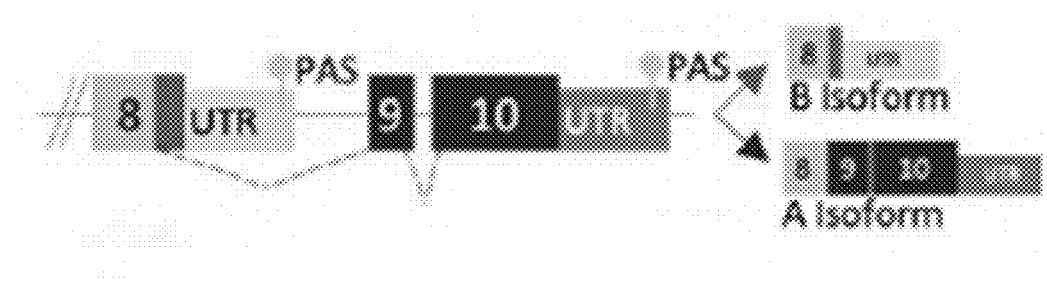
FIG. 2A shows a partial map of DNAJB6 gene structure and two DNAJB6 transcripts generated by competition between alternative splicing and polyadenylation. DNAJB6a expression depends on activation of intron 8 splicing and use of a strong distal polyadenylation signal (PAS). Conversely, DNAJB6b production requires a lack of intron 8 splicing and use of a proximal, weak PAS within intron 8.
Figure 2B:
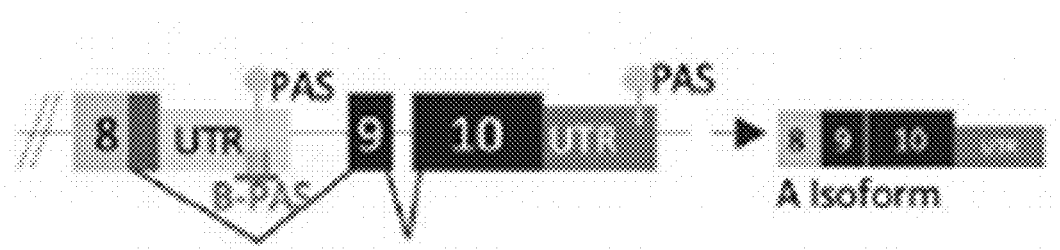
FIG. 2B shows ASO designed to reduce DNAJB6b transcript (B-PAS) targets the proximal PAS downstream of exon 8.
Figure 3A:
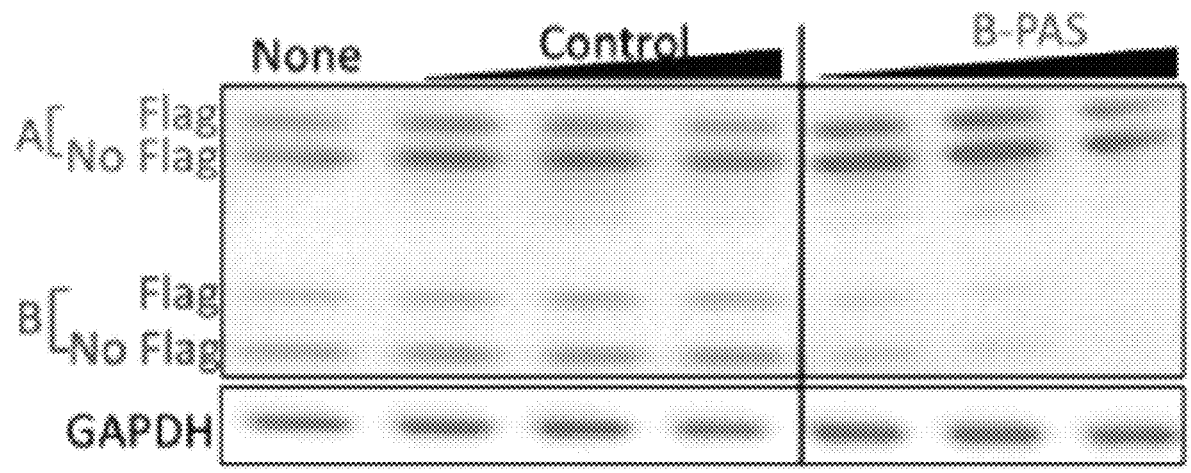
FIG. 3A shows DNAJB6 western blot from primary myotube cultures established from heterozygous F90I flag tagged knock-in mice. Two bands are present for each isoform due to the heterozygous flag tag, allowing for the detection of allele specific differences. Myotubes were incubated with ASOs at 3 different doses (2.5 µm, 5 µm, 10 µm) for 4 days prior to collection. Treatment with B-PAS selectively reduces DNAJB6b.
Figure 3B:
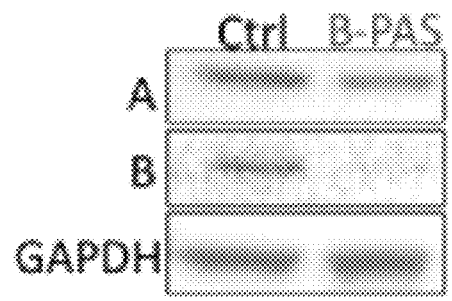
FIG. 3B shows DNAJB6 western blot of skeletal muscle lysates from C57 mice 4 days after intramuscular injection of TA muscles with ASO. Mice received B-PAS in one leg, and control ASO in contralateral leg.
Figure 4:
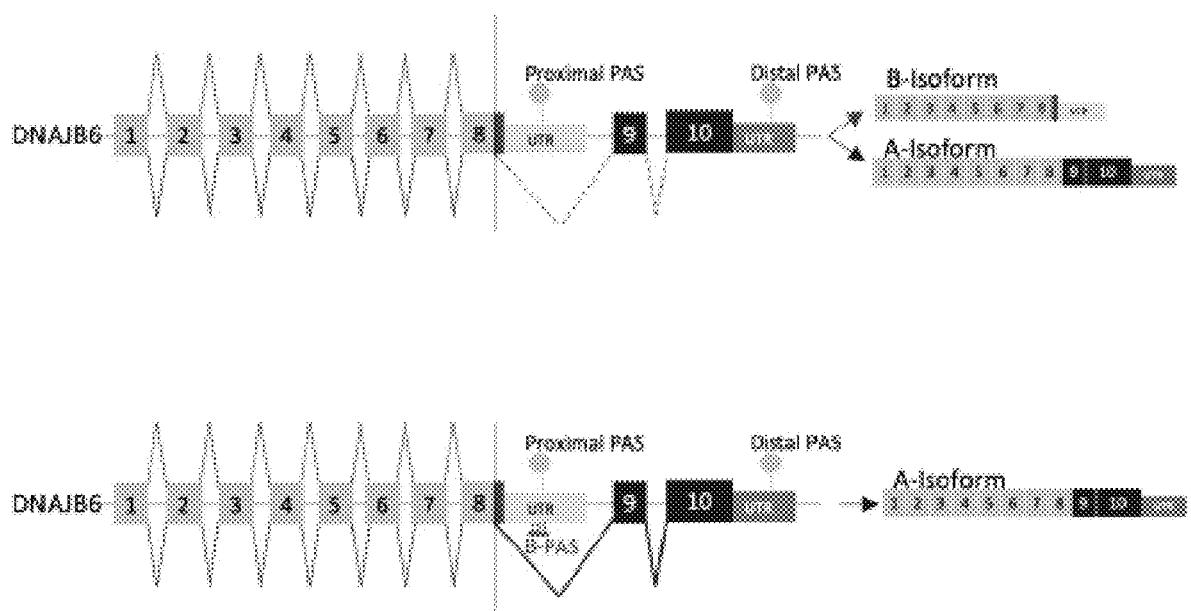
FIG. 4 depicts a map of DNAJB6 gene structure and transcripts generated by competition between alternative splicing and polyadenylation. DNAJB6a expression depends on activation of intron 8 splicing and use of a strong distal polyadenylation signal (PAS). DNAJB6b production requires a lack of intron 8 splicing and use of a proximal, weak PAS within intron 8. Morpholino designed to selectively reduce DNAJB6b transcript (B-PAS) targets the proximal PAS, sterically blocking this sequence, preventing its polyadenylation.
Figure 5A:
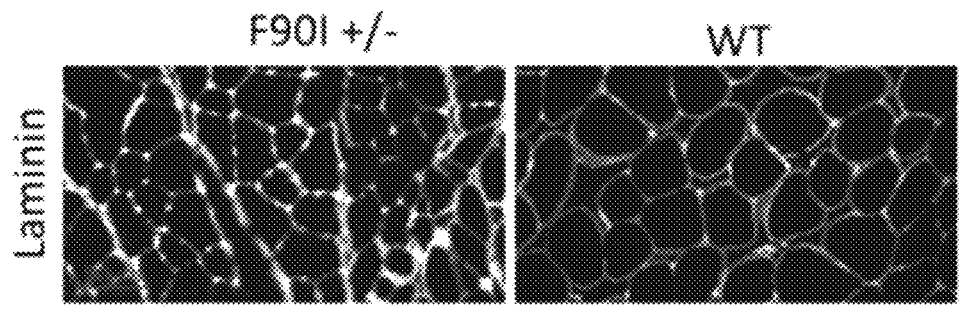
FIG. 5A shows TA muscle from 1 year old knock-in heterozygous F90I mice demonstrate mild myopathic changes.
Figure 5B:
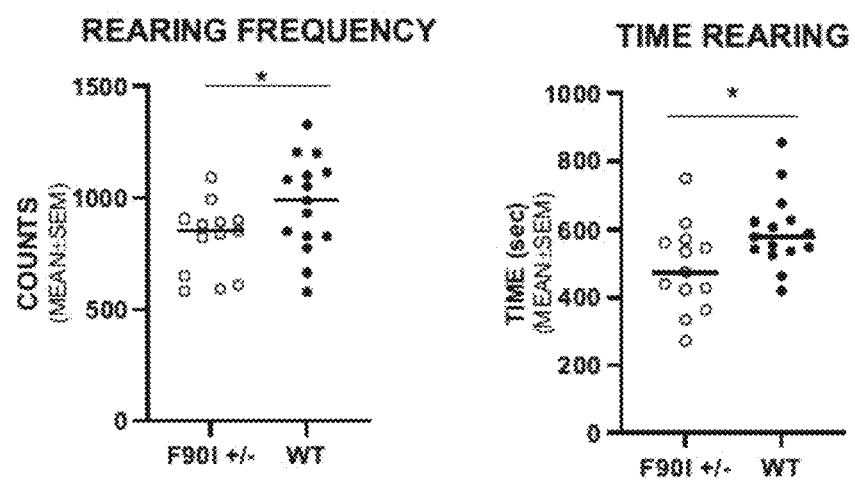
FIG. 5B shows at 7 months, F90I+/− mice have mild functional deficits in rearing frequency and total time spent rearing.
Figure 5C:
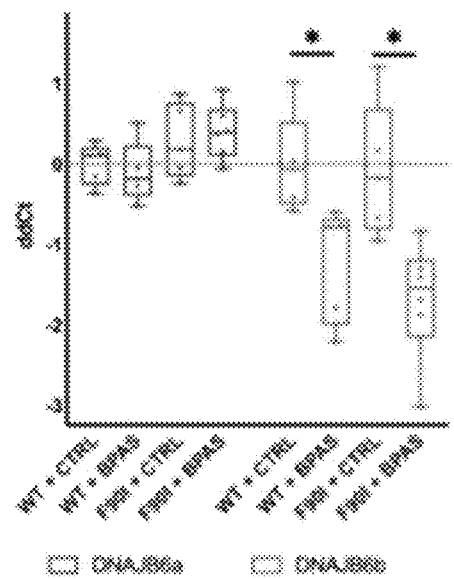
FIG. 5C shows Quantitative real time qPCR (qRT-PCR).
Figure 5D:
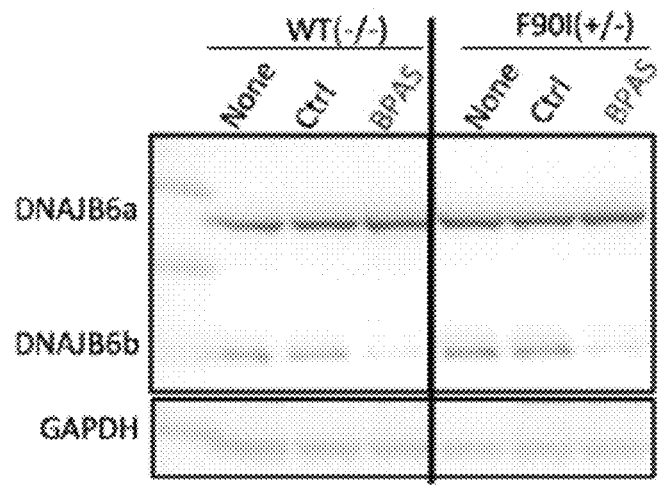
FIG. 5D shows representative western blot of WT and F90I+/− primary myotubes incubated with B-PAS morpholino at 2.5 µM for 3 days demonstrate selective reduction of DNAJB6b at both RNA and protein levels.
Figure 5E:
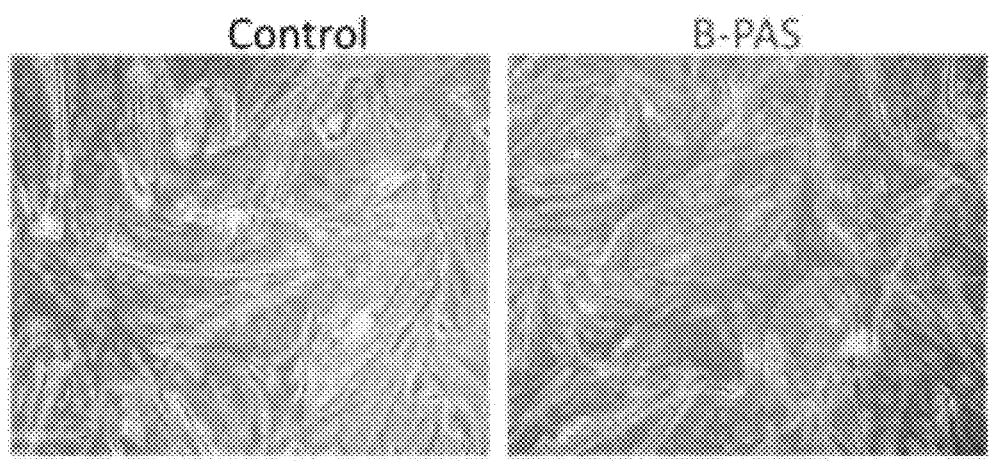
FIG. 5E shows bright field image of myotubes treated with 2.5 µM morpholino demonstrate no morphological evidence of toxicity.

DNAJB6 isoforms' roles in LGMDD1 pathogenesis: DNAJB6 has two alternatively spliced isoforms, the large isoform, DNAJB6a, localizes to the nucleus, while DNAJB6b, the short isoform, localizes to nuclei and the Z disc of muscle (FIG. 1A). Disease causing mutations reside within regions shared by both isoforms (FIG. 1A), yet several lines of evidence suggest only DNAJB6b is responsible for disease pathogenesis. This is unique, as few other disorders with isoform specific pathogenesis have been described. This mechanism is supported by transgenic mouse models, as well as zebrafish models, that develop a myopathy in the presence of mutant DNAJB6b, but not DNAJB6a (FIG. 1B and FIG. 1C). Additionally, it has recently been shown that genetic and pharmacologic inactivation of mutant DNAJB6b rescues LGMDD1 phenotypes in vitro and in vivo. Therefore, the present example provides that reducing DNAJB6b isoform expression will improve strength and pathology in LGMDD1 (FIG. 2). Reducing DNAJB6b via global knockdown of both isoforms carries risk and may not be therapeutic in LGMDD1 as knockout results in embryonic lethality. Traditional methods to selectively target DNAJB6b, such as siRNA, are not feasible due to its near complete sequence identity to DNAJB6a (FIG. 1A and FIG. 2), and its significant similarity to other DNAJ paralogues. Therefore, therapeutically modulating DNAJB6b isoform levels is challenging and requires an innovative and original approach. Regulation of DNAJB6 isoform expression involves a complex mechanism of competition between splicing and alternative polyadenylation to specify terminal exon usage (FIG. 2), similar to IgM heavy chain switching from membrane bound to a secreted isoform. Although uncommon, this mechanism lends itself to manipulation using antisense oligonucleotides (ASOs). In fact, therapeutic targeting of isoform expression via ASOs is an emerging and promising area of research. Additionally, several ASO based treatments are now FDA approved for neuromuscular disorders. To test potential therapeutic ASOs two different knock-in LGMDD1 mouse models are used, both have heterozygous F90I mutations, and one contains an additional knock-in flag tag on the wild type allele to detect allele specific differences (FIG. 3A). Additionally, LGMDD1 patient derived induced pluripotent stem cell (iPSC) lines and gene-corrected isogenic controls were generated. The present Examples provides designed ASOs that selectively reduce levels of DNAJB6b in vitro and in vivo at the protein level (FIG. 2 and FIG. 3).

Selectively reduction of DNAJB6 isoform levels to rescue LGMDD1 phenotypes: Several studies indicate DNAJB6b is responsible for disease pathology in LGMDD1 (FIG. 1C). DNAJB6 isoform expression were reduced in model systems, which include knock-in LGMDD1 mice and patient derived iPSCs, to determine the efficacy of such a therapeutic strategy (FIG. 2) ASOs were designed, optimized and screened for LGMDD1 biomarkers in mouse primary cultured myotubes treated with DNAJB6b isoform reducing ASOs. Additional ASOs screened in vitro in established primary cell cultures to identify those most effective at reducing DNAJB6b levels. LGMDD1 and control primary myotube cultures treated with the most efficient ASOs and assessed isoform levels at the RNA and protein levels. Biomarkers of chaperone dysfunction assessed via custom qPCR and immunoblot panels and compared between the different groups. Optimal dosage and duration of action determined in vivo. Control mice treated with 5 different doses of ASO via single tail vein injection and sacrificed at 4 days post injection. Skeletal muscle among other tissues collected and assessed changes in isoform levels at the mRNA and protein levels. Additional tissue collected and assessed for biodistribution. Duration of action determined by treating with the optimal dosage and collecting tissues at multiple time points (4 days, 7 days, 14 days). Phenotypic effect on LGMDD1 and control mice treated with DNAJB6b isoform reducing ASOs characterized. Control and LGMDD1 mice treated with the optimal dose and frequency determined for a period of at least 2 months. Strength assessed via grip strength and wire hang assays. Serum creatine kinase levels measured during the course of treatment. DNAJB6 isoform levels assessed at RNA and protein levels following treatment. Skeletal muscle pathology assessed via routine histochemical stains and muscle fiber cross sectional area quantified as previously done. RNA sequencing performed on skeletal muscle to screen biomarkers correlating with changes in DNAJB6b levels. Candidates validated via qPCR and immunoblot analysis. Off target changes in splicing also assessed via RNAseq.

FIG. 5 provides morpholino reduces DNAJB6b transcript and Protein in cultured primary myotubes.

Figure 6A:
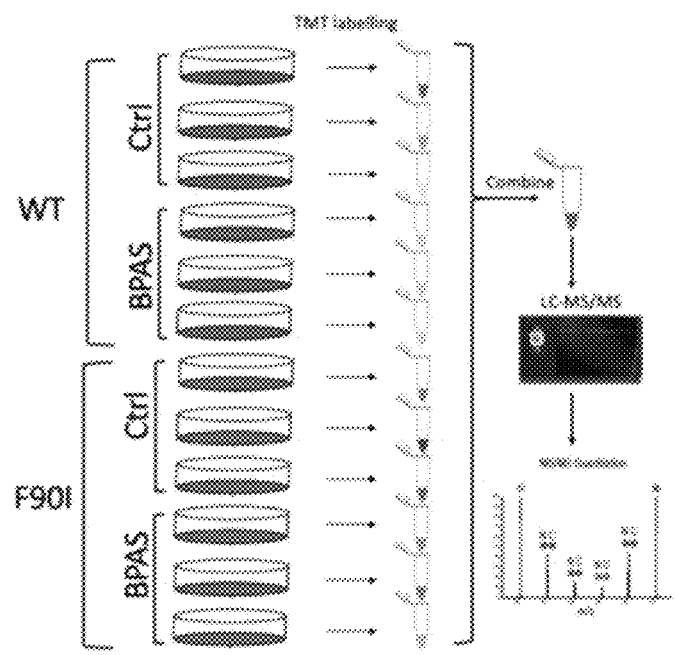
FIG. 6A shows experimental setup for proteomic analysis. Triplicates of WT and F90I myotubes treated with control or B-PAS morpholino were collected and TMT labelled for multiplexed LC-MS/MS analysis.
Figure 6B:
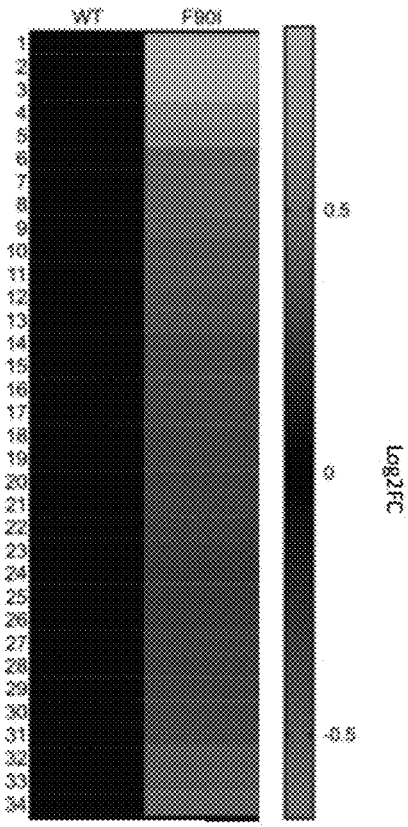
FIG. 6B shows Log2FC heatmap of 34 proteins with significant differences in abundance when com-pared to WT control treated myotubes (FDR<1° A, log2FC>0.25 or <−0.25, pAdj<0.05, coverage>30%, # peptides>10, # PSM>20). 34 proteins were identified in F90I myotubes and represent an LGMD-D1 proteomic signature.
Figure 6C:
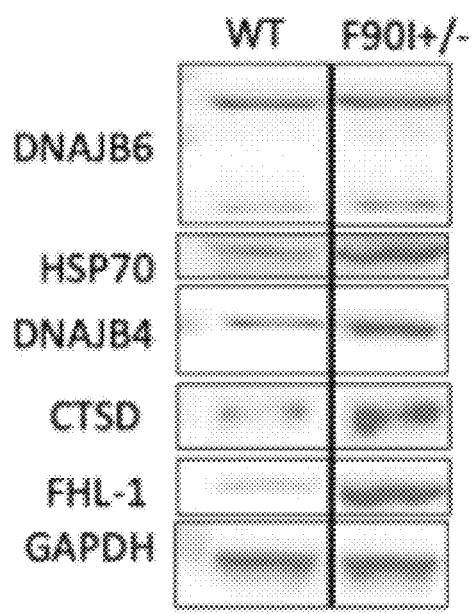
FIG. 6C shows western blot validation of several proteins identified in the LGMD-D1 proteomic signature.

FIG. 6 provides Mass spectrometry identifies disease signature in LGMD-D1 myotubes.

Figures 7A, 7B:
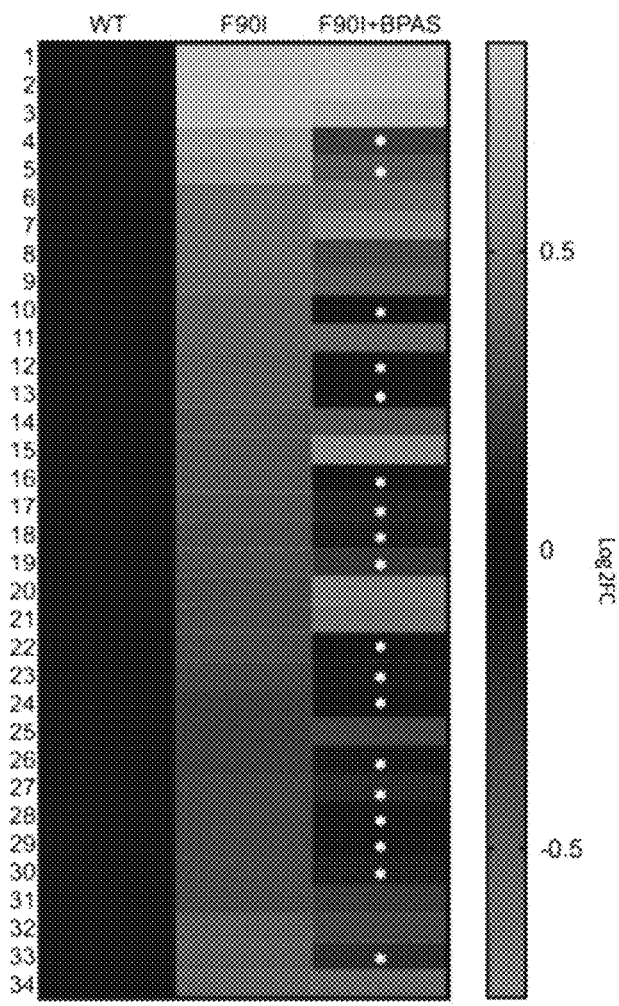
FIG. 7A shows a heatmap of LGMD-D1 proteomic signature in F90I primary myotubes treated with control or B-PAS morpholino. Data expressed as log 2 fold change relative to WT control treated myotubes. Higher abundance is indicated by more green shades, whereas less abundance is represented by red. In BPAS treated myotubes, 52% of the LGMD-D1 proteomic signature is corrected back towards WT levels. Asterisks denote the 18 proteins whose relative abundances were significantly restored to healthy levels (FDR<1° A, log2FC>0.25 or <−0.25, pAdj<0.05, coverage>30%, # peptides>10, # PSM>20).
FIG. 7B shows closest off target of B-PAS has 3 mismatches and its levels were not altered in the proteomic dataset.

FIG. 7 provides DNAJB6b Reduction Improves LGMD-D1 Disease Signature in Primary Myotubes.

Figure 8A:
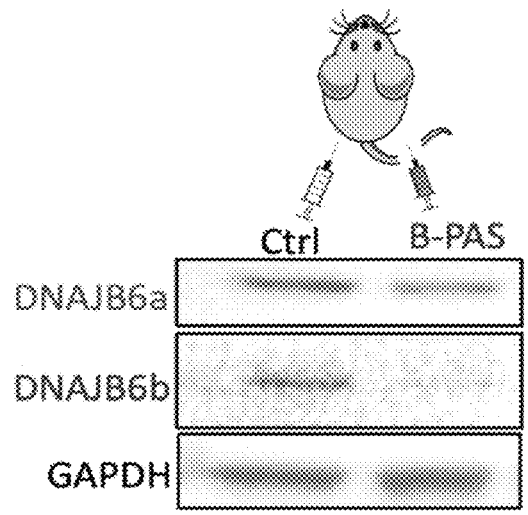
FIG. 8A shows DNAJB6 western blot of skeletal muscle lysates from C57 mice 4 days after intramuscular injection of TA muscles with morpholino. B-PAS was administered to one leg, and control morpholino to the contralateral.
Figure 8B:
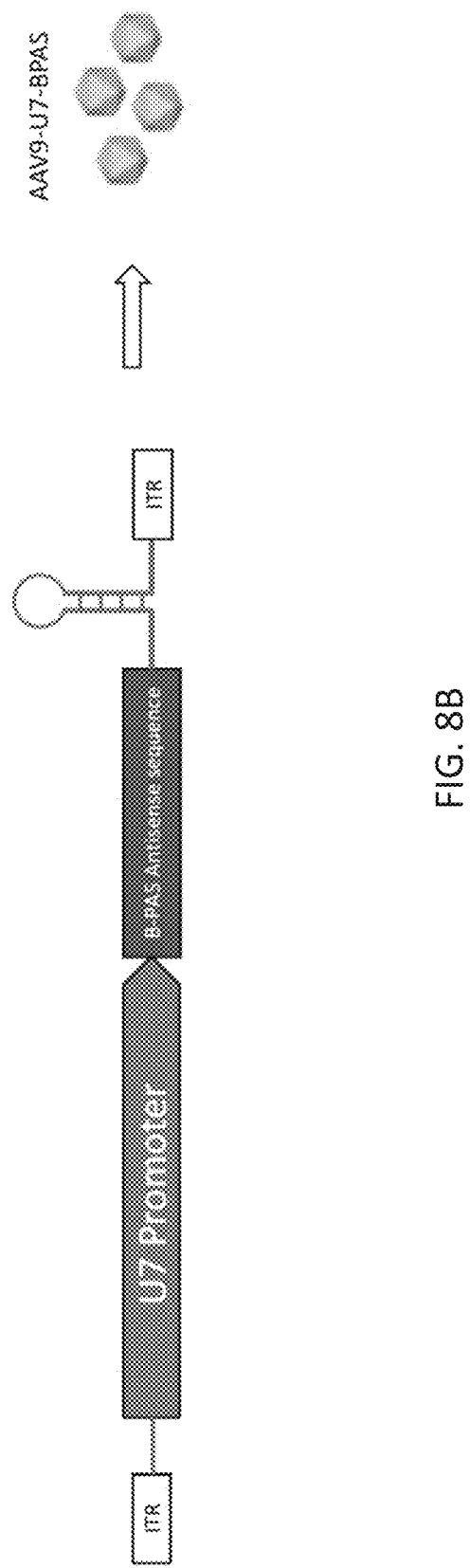
FIG. 8B shows AAV9 U7 snRNP.

FIG. 8 provides Single In-Vivo Administration of Morpholino Reduces DNAJB6b.

FIG. 9 provides Therapeutic Strategy: Allele specific knockdown Myoblasts: Knock-in F90I+/−, Flag−/+ ASOs: LNA-GapmeR.

Figure 10:
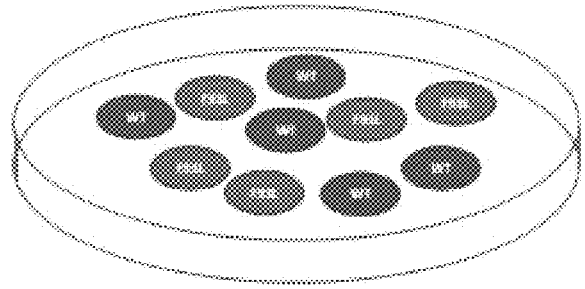
FIG. 10 shows therapeutic strategy for allele specific knockdown Stable Cells: DNAJB6b-WT-V5, DNAJB6b-F93L-GFP. (SEQ ID NOs: 7, 8, 9, 10, 11, 12, 5 and 6).

FIG. 10 provides Therapeutic Strategy: Allele specific knockdown Stable Cells: DNAJB6b-WT-V5, DNAJB6b-F93L-GFP ASOs: LNA-GapmeR.

FIG. 11 provides Therapeutic Strategy: Allele specific knockdown Stable Cells: DNAJB6b-WT-V5, DNAJB6b-F93L-GFP ASOs: LNA-GapmeR.

Figure 12:
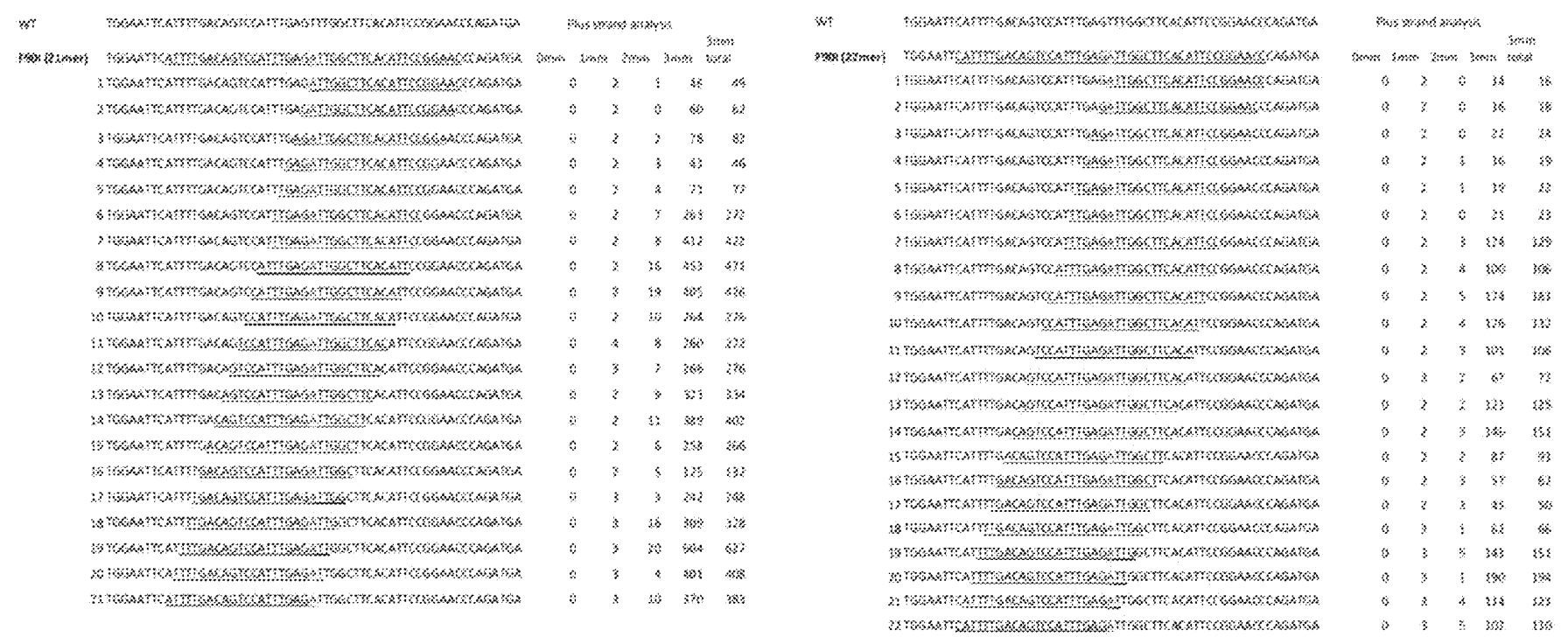

FIG. 12 provides 21mer vs 22mer siRNA Off target analysis.

Figure 13:
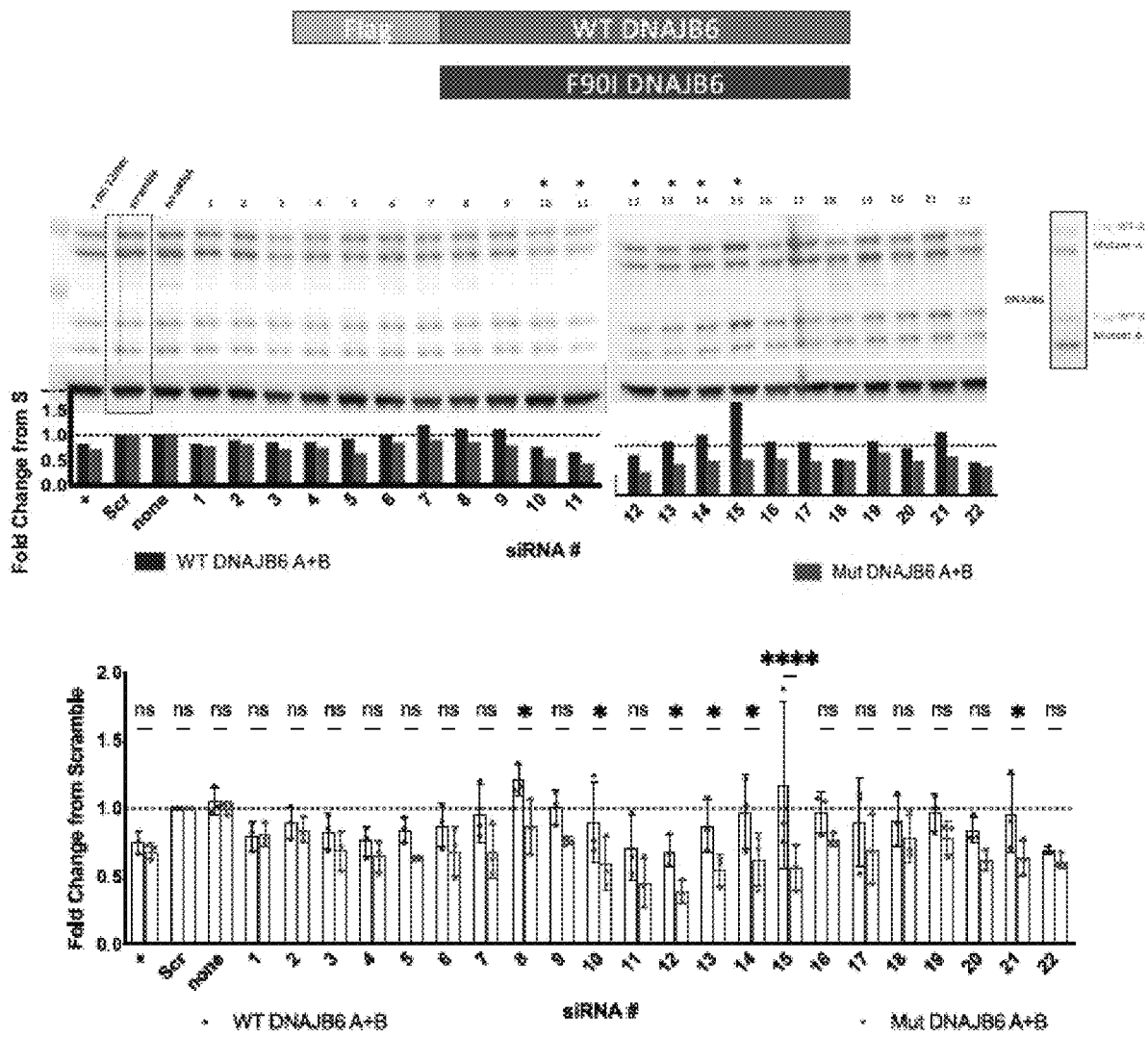
FIG. 13 shows Allele specific knockdown: siRNA.

FIG. 13 provides Allele specific knockdown: siRNA.

Figure 14:
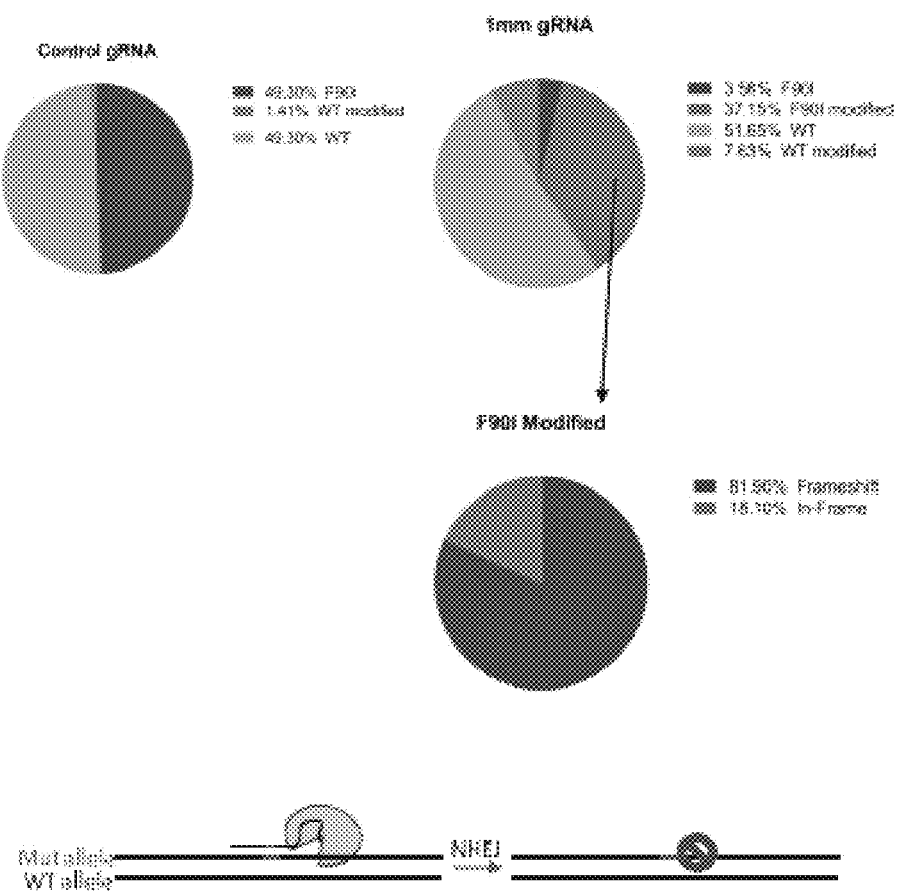
FIG. 14 shows therapeutic strategy for allele specific knockout, Myoblasts: knock-in F90I+/−, CRISPR/Cas9: NHEJ (active in non-dividing cells).
Figure 16:
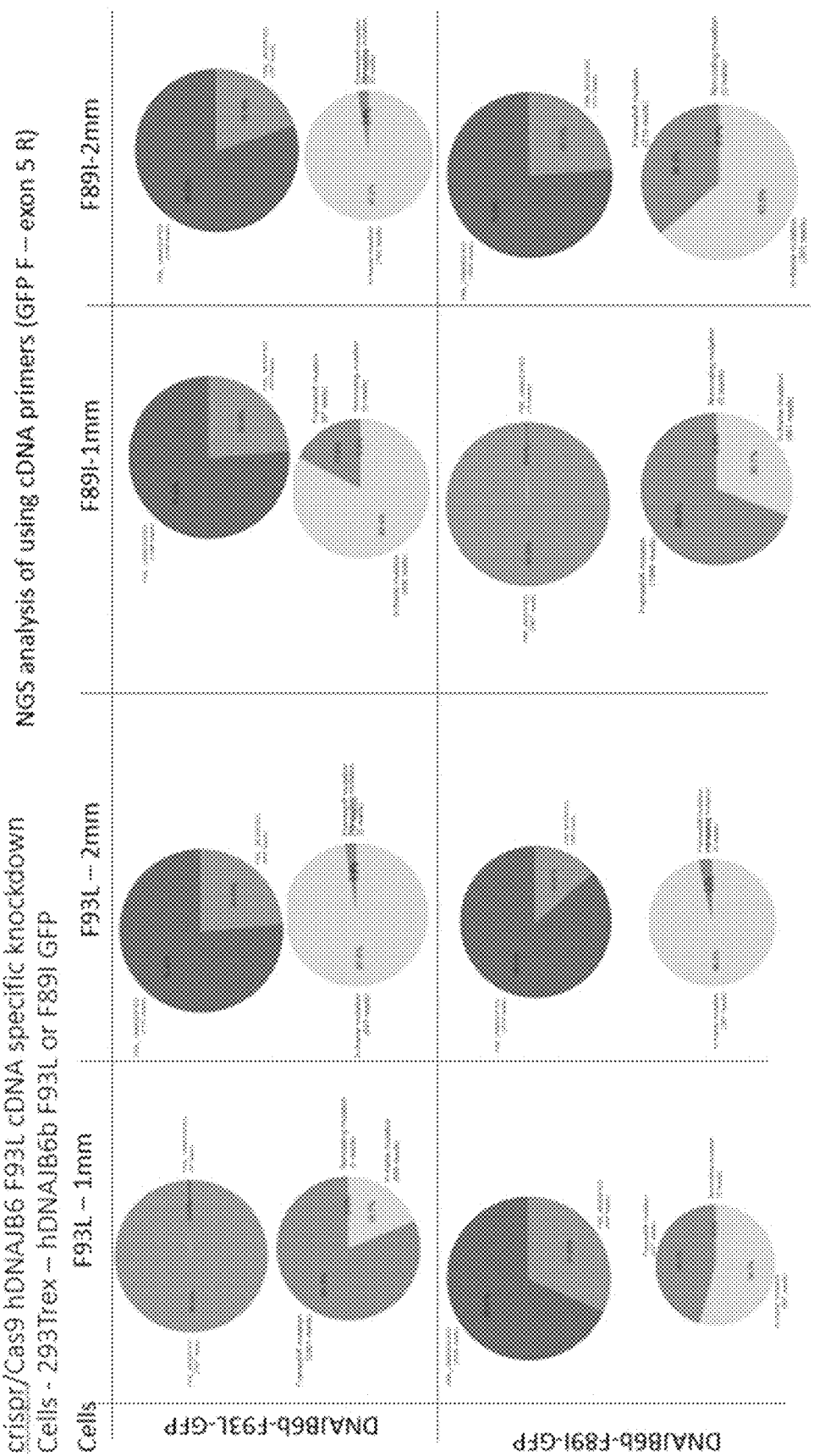
FIG. 16 shows NGS analysis of using cDNA primers (GFP F—exon 5 R).
Figure 17A:
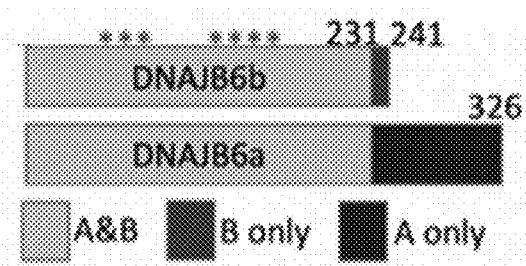
FIG. 17A shows a map of DNAJB6 isoforms and disease-causing mutations (asterisks).
Figure 17B:
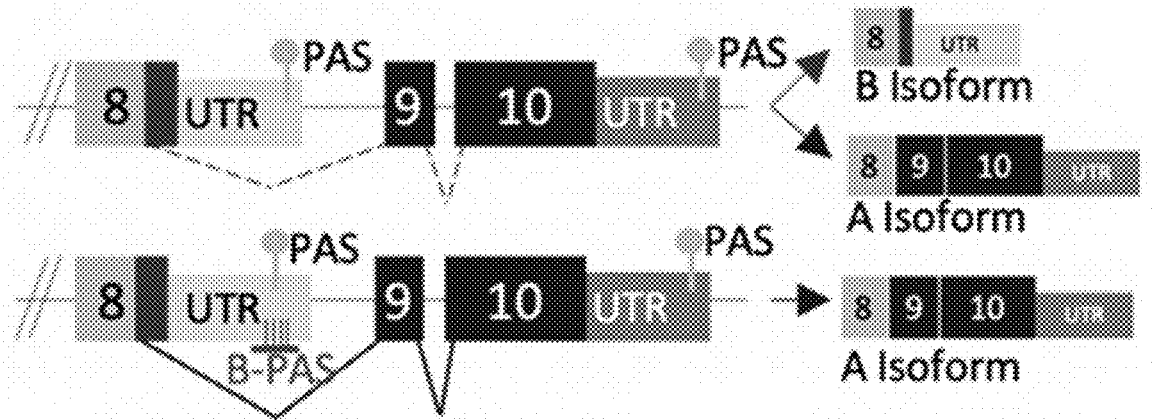
FIG. 17B shows a partial map of DNAJB6 gene structure and two DNAJB6 transcripts generated by competition between alternative splicing and polyadenylation. DNAJB6b production requires a lack of intron 8 splicing and use of a proximal, weak PAS within intron 8.12 ASO designed to reduce DNAJB6b transcript (B-PAS) targets the proximal PAS downstream of exon 8.
Figure 17C:
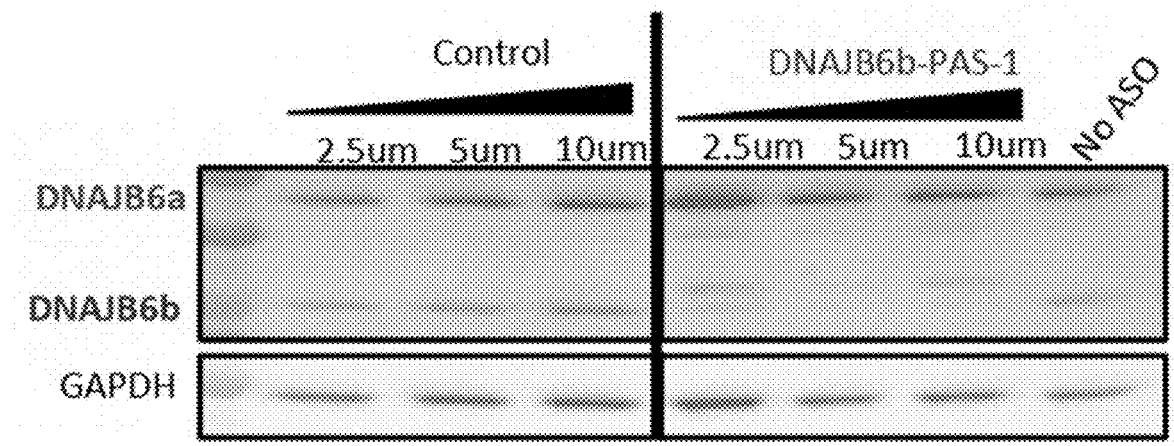
FIG. 17C shows DNAJB6 western blot from primary mouse myotube cultures. Myotubes were incubated with ASOs for 4 days. B-PAS treatment selectively reduces DNAJB6b.
Figure 18A:
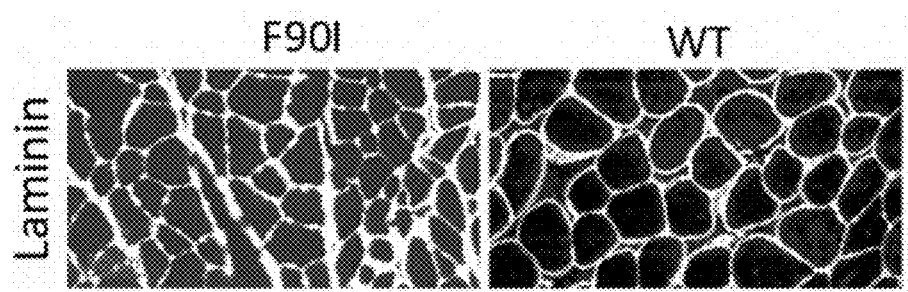
FIG. 18A shows LGMDD1 mouse model containing knock-in heterozygous F90I mutation has myopathic changes demonstrated by laminin staining of skeletal muscle from 7-month-old mice.
Figure 18B:
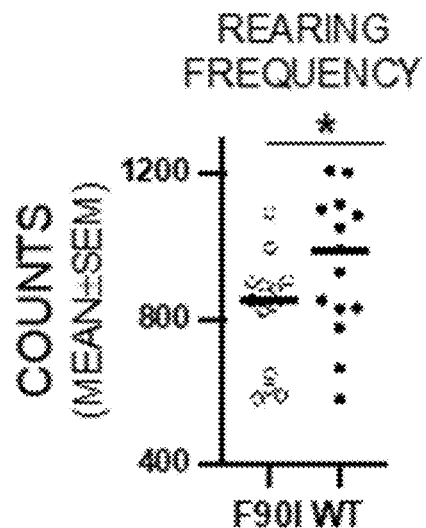
FIG. 18B shows the frequency of rearing (standing on hind legs) is reduced in F90I mice.
Figure 18C:
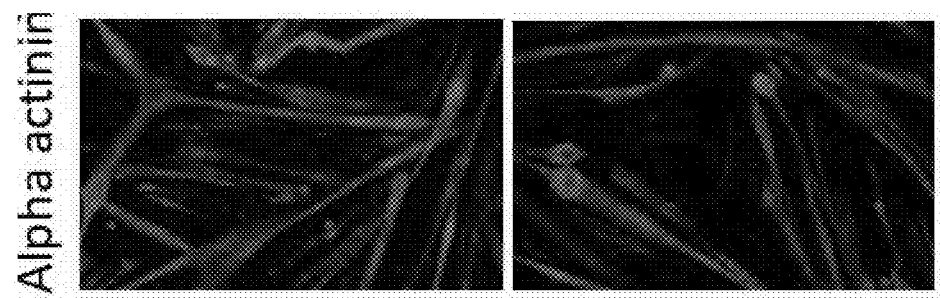
FIG. 18C shows primary myotube cultures established from F90I and WT mice stained for alpha actinin, and have no difference in fusion index.
Figure 18D:
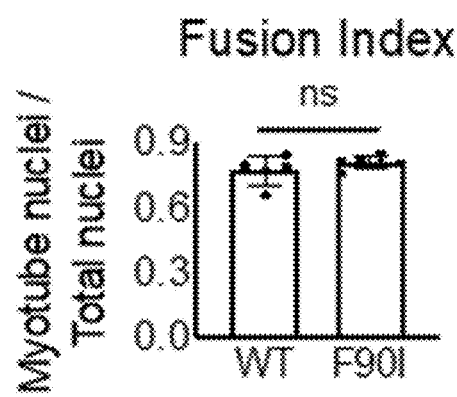
FIG. 18D shows the fusion index.
Figure 18E:
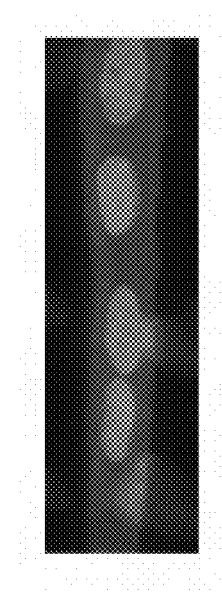
FIG. 18E shows Human iPSCs differentiated into skeletal muscle (14 days). Myosin heavy chain (green), TDP-43 (red).
Figure 18F:
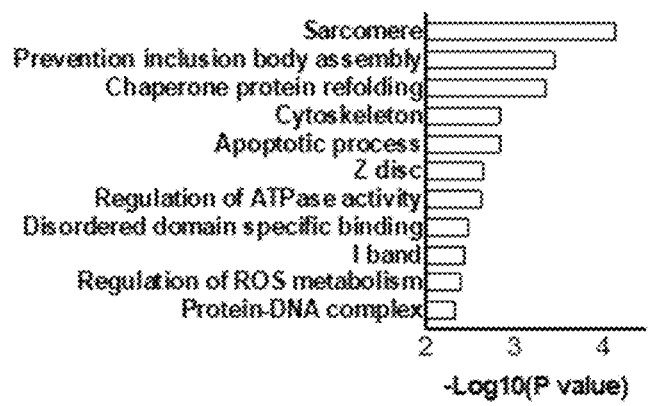
FIG. 18F shows ontological analysis of LGMDD1 proteomic disease signature.
Figure 18G:
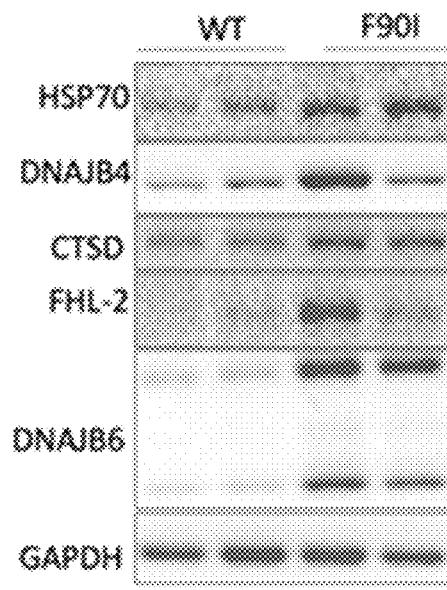
FIG. 18G western blot validation of several proteins within profile.
Figure 19A:
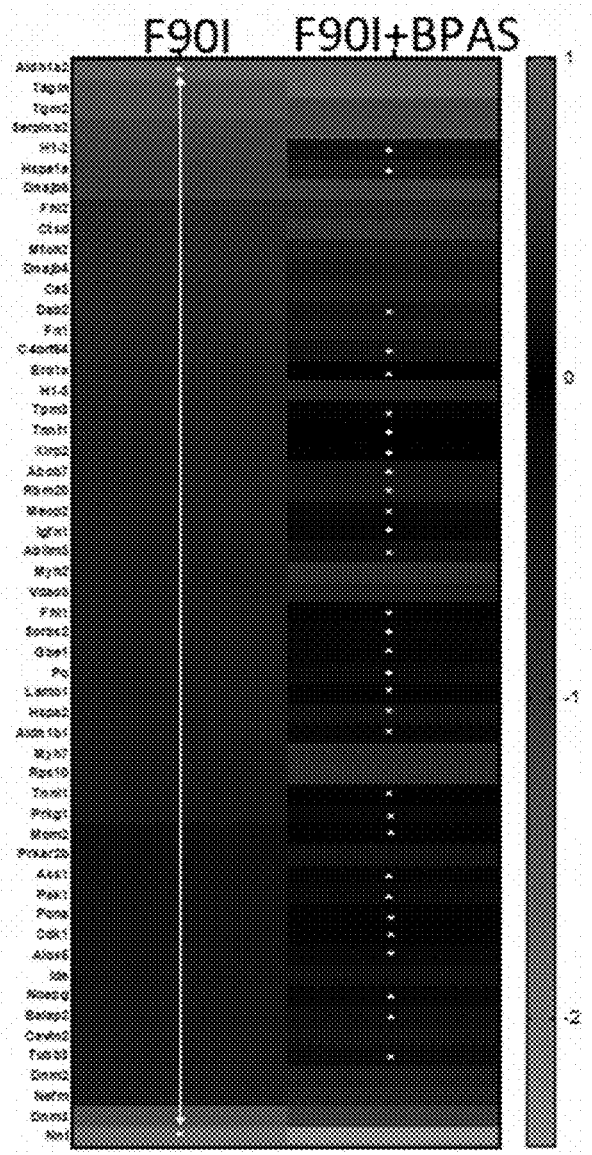
FIG. 19A shows Log2FC heatmap of 54 proteins with altered abundance in F90I myotubes. Following DNAJB6b reduction in F90I myotubes for 6 days, 31/54 (57%) proteins returned to WT levels.
Figure 19B:
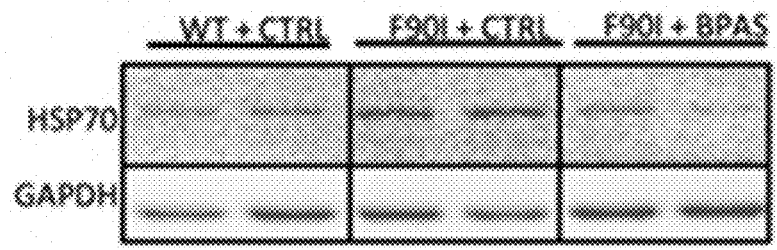
FIG. 19B shows western blot validation of HSP70 normalization following DNAJB6b reduction.
Figure 19C:
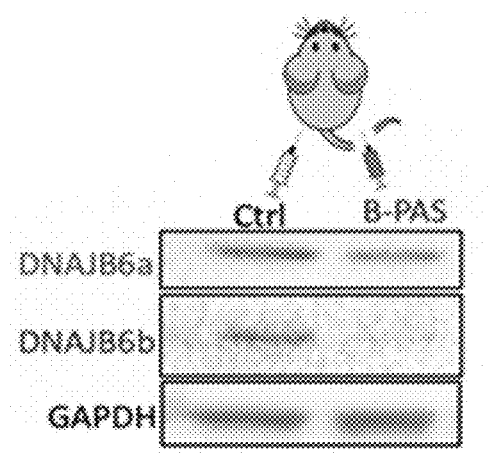
FIG. 19C shows DNAJB6 western blot of skeletal muscle lysates from C57 mice 4 days after IM injection of TA muscles with BPAS.
Figure 19D:
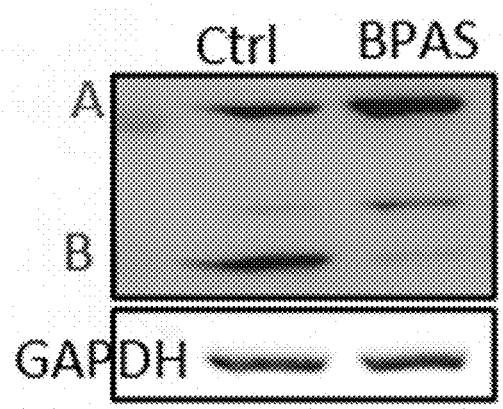
FIG. 19D shows primary human LGMDD1 myoblasts treated with BPAS.
Figure 20A:
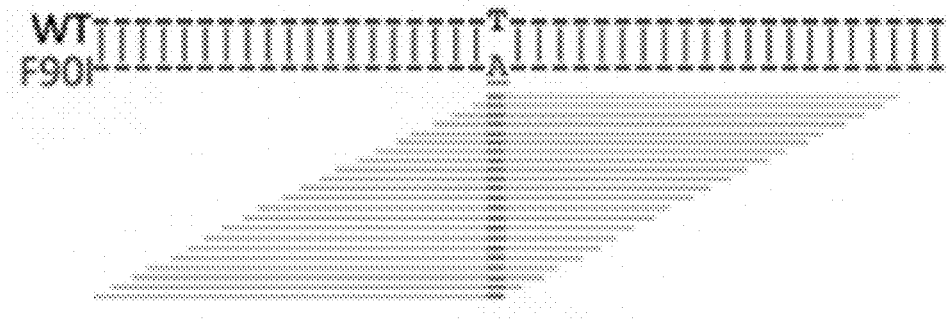
FIG. 20A shows siRNAs are systematically designed by tiling them across the mutation site.
Figure 20B:
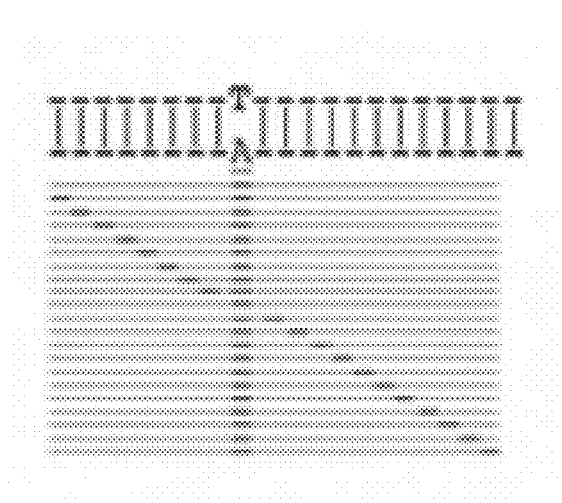
FIG. 20B shows after selecting an ideal candidate, a 2nd mismatch is tiled along the siRNA to improve specificity for the mutant.
Figure 20C:
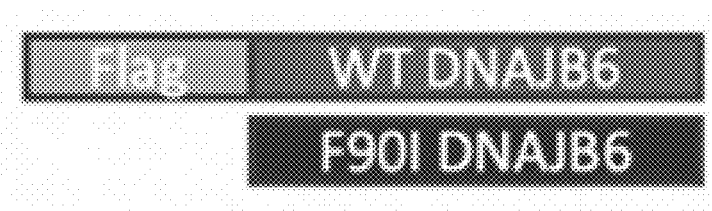
FIG. 20C shows color coded schematic of WT-Flag and mutant DNAJB6 alleles in double knock-in LGMDD1-Flag mouse model.
Figure 20D:
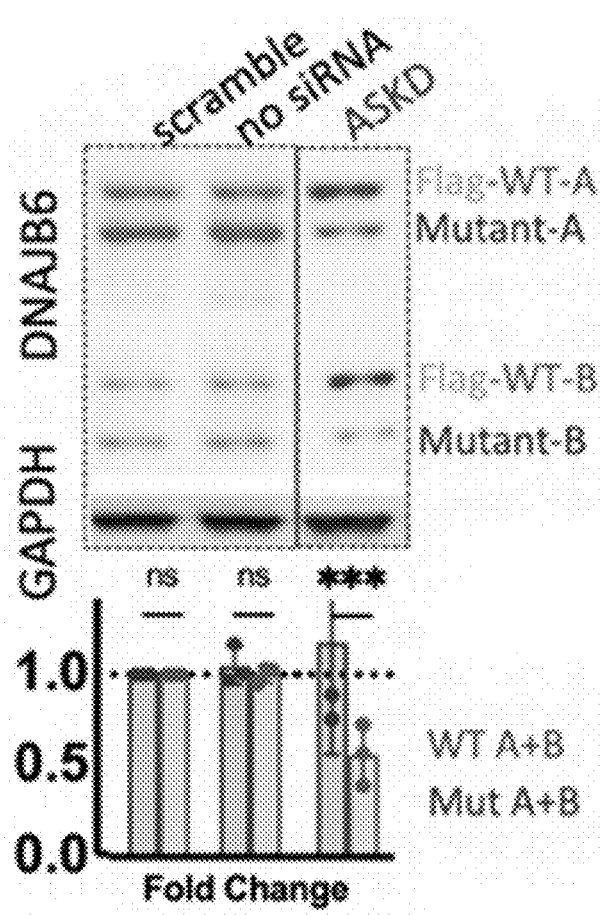
FIG. 20D shows western blot of LGMDD1 flag myotubes treated with siRNA. ASKD lane is best siRNA from 1st screening step (A), demonstrating selective reduction of mutant DNAJB6, quantitated as fold change from scramble.
Figure 21A:
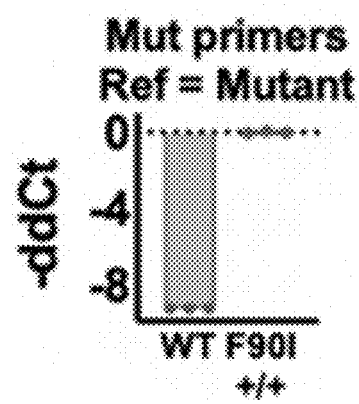
FIG. 21A shows allele specific RTqPCR using primers specific for mutant (F90I) DNAJB6. Compared to cells homozygous for F90I mutation, there is 2e9 fold less signal in the WT cell line.
Figure 21B:
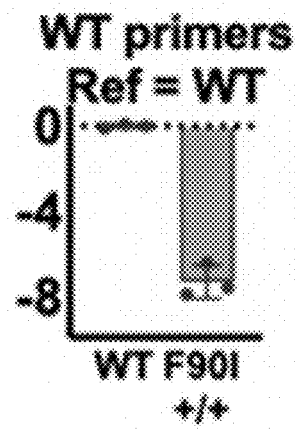
FIG. 21B shows using WT specific primers, and WT cells as reference, we see 2e7 fold less signal in the homozygous F90I mutant line.
Figure 21C:
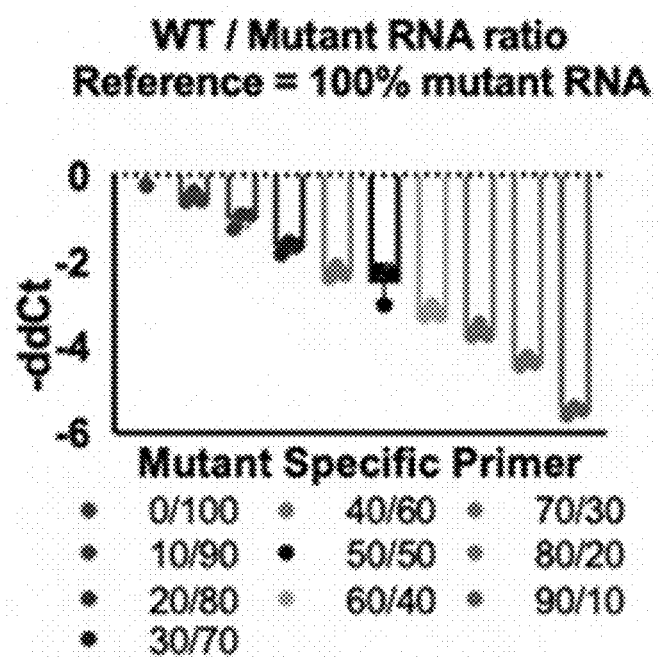
FIG. 21C shows titration experiment using F90I mutant specific primers and varying ratios of WT RNA mixed with homozygous F90I RNA, demonstrating allele specific primers are capable of detecting even small 10% changes in mutant transcript levels. Signal undetectable at 100% WT RNA.

FIG. 14 provides CRISPR/Cas9 allele targeting.

Limb-Girdle Muscular Dystrophy type D1 (LGMDD1) is an ultra-rare autosomal dominantly inherited muscular dystrophy that affects ~200 patients in the US. LGMDD1 is due to toxic gain of function mutations in the HSP40 co-chaperone DNAJB6. Current treatment is supportive and the disease course is progressive and disabling with patients losing ambulation 20-30 years after onset.

Previous work has generated several LGMDD1 mouse models that recapitulate key features of the human disease including weakness and muscle pathology. These models have allowed us to understand the pathogenic mechanism of DNAJB6 mutations and identify potential therapeutic targets. In addition to a gain of function, there is an isoform specific component to the pathomechanism: the small DNAJB6b isoform which localizes to myofibrillar structures in muscle is responsible for disease. The present example provides that two approaches have therapeutic potential: 1) Isoform specific knockdown of DNAJB6b and 2. Targeted knockdown of the mutant allele.

Due to differences in isoform sizes, the ability to measure endogenous DNAJB6b isoform knockdown in LGMDD1 mice is feasable. However, in order to detect selective knockdown of the mutant allele, mice carrying allele specific tags were generated. To facilitate translation to humans, LGMDD1 patient derived iPSC myoblasts and their isogenic controls were created. An LGMDD1 disease specific proteomic biomarker was also identified. Using these tools, antisense drugs that preferentially decrease mutant DNAJB6 (siRNA) or effectively knockdown the DNAJB6b isoform in myotube cultures (morpholino) have been generated.

Although gene-based therapies are becoming a reality for disabling neuromuscular diseases, the field has focused almost entirely on recessive disorders. Gene replacement strategies employed for recessive, loss of function disorders are not translatable to most dominant muscular dystrophies, leaving them far behind in the path towards a cure. Recently mutations in DNAJB6 have been identified which cause limb girdle muscular dystrophy D1 (LGMDD1), a childhood onset, disabling, dominantly inherited myopathy with myofibrillar pathology. No treatments are available. Standard of care is supportive in nature (physical therapy, wheelchairs, etc). No commercial programs are focused on LGMDD1. However, as viral vectors and RNAi based therapies have become clinical realities, the key tools are now in place to develop a treatment for LGMDD1.

LGMDD1 Disease Mechanisms: Isoform Specific Toxic Gain of Function: DNAJB6 is a ubiquitously expressed HSP-40 co-chaperone that facilitates protein folding. It has two isoforms with distinct subcellular localizations. DNAJB6a localizes to myonuclei while DNAJB6b localizes to myofibrillar structures, the key site of pathology seen in patient biopsies. Both isoforms contain the domains where disease causing mutations reside. Several lines of evidence indicating DNAJB6 mutations exert a dominant effect through a toxic gain of function, specifically involving the DNAJB6b isoform. Complete knockdown might seem like a good therapeutic approach. However, absence of DNAJB6 is embryonic lethal. Interestingly, DNAJB6 haploinsufficiency is tolerated. Two different approaches have therapeutic potential for LGMDD1:1. Isoform specific knockdown of DNAJB6b and 2. Targeted knockdown of the mutant allele. Both address the toxic gain of function mechanism, yet avoid the damaging effects of complete DNAJB6 knockout.

Selectively reduce DNAJB6b isoform levels to rescue LGMDD1 phenotypes: Regulation of DNAJB6 isoform expression involves a competition between splicing and alternative polyadenylation to specify terminal exon usage. This mechanism lends itself to manipulation using antisense oligonucleotides (ASOs). For proof of concept, morpholinos were designed, a subset of ASO, to successfully reduce DNAJB6b by sterically blocking its polyadenylation signal. A knock-in LGMDD1 mouse model containing a heterozygous F90I mutation (orthologous to human F89I mutation) was used to test ASOs. These mice develop a myopathy evident on histopathology and functional testing at approximately 7 months of age. Primary myotube cultures from these mice were also used. Although myotube cultures from LGMDD1 mice do not have any obvious phenotypic differences (myotube diameter or fusion index), 54 proteins with altered abundances using mass-spectrometry were identified. Ontological analysis supports their relevance to disease pathogenesis involving protein homeostasis of myofibrillar proteins. Several proteins of particular relevance on western blot. This group of proteins can be considered as a disease signature. To assess the efficacy and specificity of DNAJB6b isoform knockdown, LGMDD1 mouse myotubes were treated with the ASO for 6 days and found 31 of the 54 disease profile proteins (57%) normalized back to WT levels. Western blot validation of the protein most relevant to disease pathogenesis, HSP70, confirmed its levels normalize following treatment. Off target binding appears minimal as the closest off-target gene has 3 mismatches, and its expression levels were not changed. For preliminary in vivo testing a single IM injection in mice was found effectively reduced the B isoform. To assess human DNAJB6, several LGMDD1 patient derived iPSC lines (F89I, F93L, P96R) were generated as well as their gene corrected isogenic controls. Morpholinos effectively reduce the DNAJB6b isoform in these human cell culture models.

Tools developed for testing allele specific knockdown (ASKD) in LGMDD1: To assess allele specific differences, a flag-tagged LGMDD1 mouse was created. This model is heterozygous for an F90I mutation, with a 3× flag tag on the WT allele. This model allows for easy readout of endogenous allele specific changes at the protein level via size differences. a set of 22 siRNAs that sequentially tile across the targeted F90I point mutation were designed and have now identified several siRNA candidates capable of allele specificity to be optimized further. To identify siRNAs capable of mutant DNAJB6 ASKD in humans, the mutant iPSCs and isogenic controls were used.

AAV to deliver siRNAs using an miRNA shuttle construct was used to assess ASKD's ability to prevent and correct disease phenotypes in mice. Human: Using ideal siRNA candidates mutant iPSC myotubes were treated and assessed for normalization of all disease phenotypes.

What is claimed is:

1. A method of selectively reducing DNAJB6 in a human subject in need thereof having limb girdle muscular dystrophy D1 (LGMD), comprising administering to the subject an amount of a DNAJB6-targeting antisense oligonucleotide (ASO) sufficient to reduce DNAJB6 expression compared to DNAJB6 expression prior to being administered the DNAJB6-targeting ASO, wherein the ASO targets a proximal polyadenylation signal (PAS) downstream of exon 8 of a DNAJB6 gene.

2. The method of claim 1, wherein the ASO selectively reduces or eliminates pathogenic DNAJB6 isoform expression without significantly modulating expression of a non-pathogenic DNAJB6 isoform.

3. The method of claim 2, wherein the ASO increases intron 8 splicing of DNAJB6 or decreases expression of a DNAJB6 encoding a mutation.

4. The method of claim 1, wherein the ASO comprises the sequence TGCACCAAACACATTCGCATTTATT (SEQ ID NO: 1); or
a sequence at least about 85%, 90%, 95%, or 99% identical to SEQ ID NO: 1 having pathogenic isoform transcript reducing activity.

5. The method of claim 1, wherein the ASO targets 8-25 consecutive nucleotides within SEQ ID NO: 2, 7, 8, 9, 10, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or 56.

6. The method of claim 1, wherein the ASO targets 8-25 consecutive nucleotides with at least 90%, 91%, 92%, 93%, 94%, 95%, 96%, 97%, 98%, or at least 99% sequence identity to the 8-25 consecutive nucleotides SEQ ID NO: 2, 7, 8, 9, 10, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or 56.

7. A method of treating limb girdle muscular dystrophy D1 (LGMD) in a human subject in need thereof, the method comprising administering to the subject an amount of a DNAJB6-targeting antisense oligonucleotide (ASO) sufficient to reduce DNAJB6 expression compared to DNAJB6 expression prior to being administered the DNAJB6-targeting ASO, wherein the ASO selectively reduces or eliminates pathogenic DNAJB6 allele expression without significantly modulating expression of a non-pathogenic DNAJB6 allele, wherein the ASO targets a proximal polyadenylation signal (PAS) downstream of exon 8 of a DNAJB6 gene.

8. The method of claim 7, wherein the expression of DNAJB6a expression is unchanged or not significantly changed after administration of the ASO.

9. The method of claim 7, wherein the ASO increases intron 8 splicing of DNAJB6.

10. The method of claim 7, wherein the ASO comprises the sequence TGCACCAAACACATTCGCATTTATT (SEQ ID NO: 1); or
a sequence at least about 85%, 90%, 95%, or 99% identical to SEQ ID NO: 1 having pathogenic isoform transcript reducing activity.

11. The method of claim 7, wherein the ASO targets 8-25 consecutive nucleotides within SEQ ID NO: 2, 7, 8, 9, 10, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or 56.

12. The method of claim 7, wherein the ASO targets 8-25 consecutive nucleotides with at least 90%, 91%, 92%, 93%, 94%, 95%, 96%, 97%, 98%, or at least 99% sequence identity to the 8-25 consecutive nucleotides SEQ ID NO: 2, 7, 8, 9, 10, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or 56.

* * * * *